United States Patent [19]
Hartman et al.

[11] Patent Number: 6,001,604
[45] Date of Patent: Dec. 14, 1999

[54] REFOLDING OF PROINSULINS WITHOUT ADDITION OF REDUCING AGENTS

[75] Inventors: Jacob R. Hartman, Holon; Simona Mendelovitz, Tel Aviv; Marian Gorecki, Rehovot, all of Israel

[73] Assignee: Bio-Technology General Corp., Iselin, N.J.

[21] Appl. No.: 08/967,867

[22] Filed: Nov. 12, 1997

Related U.S. Application Data

[63] Continuation of application No. 08/367,454, Dec. 29, 1994, abandoned, which is a continuation-in-part of application No. 08/175,298, Dec. 29, 1993, abandoned.

[51] Int. Cl.⁶ ............................. C07K 1/107; C07K 1/36
[52] U.S. Cl. .................. 435/69.4; 435/69.7; 435/68.1; 530/430; 530/412
[58] Field of Search .................. 435/69.4, 69.7, 435/68.1; 530/430, 412

[56] References Cited

U.S. PATENT DOCUMENTS

| | | |
|---|---|---|
| H245 | 4/1987 | Bahl . |
| 3,420,810 | 1/1969 | Katsoyannis et al. . |
| 3,847,893 | 11/1974 | Brandenburg et al. . |
| 4,014,861 | 3/1977 | Geiger et al. . |
| 4,338,397 | 7/1982 | Gilbert et al. . |
| 4,421,685 | 12/1983 | Chance et al. . |
| 4,430,266 | 2/1984 | Frank . |
| 4,431,740 | 2/1984 | Bell et al. . |
| 4,440,859 | 4/1984 | Rutter et al. . |
| 4,569,791 | 2/1986 | Frank et al. . |
| 4,616,078 | 10/1986 | DiMarchi et al. . |
| 4,704,362 | 11/1987 | Itakura et al. . |
| 4,792,602 | 12/1988 | Narang et al. . |
| 4,916,212 | 4/1990 | Markussen et al. . |
| 4,999,422 | 3/1991 | Galliher et al. . |
| 5,015,575 | 5/1991 | Brake et al. . |
| 5,149,777 | 9/1992 | Hansen et al. . |
| 5,342,921 | 8/1994 | Cousens et al. . |

FOREIGN PATENT DOCUMENTS

| | | |
|---|---|---|
| 48620/90 | 7/1990 | Australia . |
| 45283 | 9/1983 | Denmark . |
| 0037723 | 10/1981 | European Pat. Off. . |
| 0055945 | 7/1982 | European Pat. Off. . |
| 0264250 | 4/1988 | European Pat. Off. . |
| 0036776 | 5/1988 | European Pat. Off. . |
| 0055942 | 6/1988 | European Pat. Off. . |
| 0347781 | 12/1989 | European Pat. Off. . |
| 0347845 | 12/1989 | European Pat. Off. . |
| 0108787 | 4/1990 | European Pat. Off. . |
| 0379162 | 7/1990 | European Pat. Off. . |
| 0245267 | 11/1990 | European Pat. Off. . |
| 0195691 | 11/1991 | European Pat. Off. . |
| WO8601540 | 3/1986 | WIPO . |
| WO9103550 | 3/1991 | WIPO . |

OTHER PUBLICATIONS

Scopes, R. (1982) *Protein Purification: Principles of Practice*, New York: Springer–Verlag, pp. 25–30, 81–84, 139–141, 182–183.

*Primary Examiner*—David L. Fitzgerald
*Attorney, Agent, or Firm*—John P. White; Cooper & Dunham LLP

[57] ABSTRACT

An improved and efficient process for the production of recombinant human insulin by folding of a proinsulin hybrid polypeptide is provided.

13 Claims, 14 Drawing Sheets

FIGURE 6

(SEQ. ID. NO. 5)

```
  1   Met Ala Thr Lys Ala Ala Ser Val Leu Lys Gly Asp Gly Pro Val Gln    16
  1   ATG GCT ACT AAA GCC GCT AGC GTG CTG AAG GGC GAC GGC CCA GTG CAG    48

17   Gly Ile Ile Asn Phe Glu Gln Lys Glu Ser Asn Gly Pro Val Lys Val    32
 49   GGC ATC ATC AAT TTC GAG CAG AAG GAA AGT AAT GGA CCA GTG AAG GTG    96

33   Trp Gly Ser Ile Lys Gly Leu Thr Glu Gly Leu His Gly Phe His Val    48
 97   TGG GGA AGC ATT AAA GGA CTG ACT GAA GGC CAT GGA TTC CAT ATT       144

49   His Glu Phe Gly Asp Asn Thr Ala Gly Ser Thr Ser Ala Gly Pro Arg    64
145   CAT GAG TTT GGA GAT AAT ACA GCA GGC AGT ACT AGT GCA GGT CCT CGT   192

65   Phe Val Asn Gln His Leu Cys Gly Ser His Leu Val Glu Ala Leu Tyr    80
193   TTT GTC AAC CAG CAC CTG TGT GGT TCT CAC CTA GTT GAA GCA CTG TAC   240

81   Leu Val Cys Gly Arg Gly Phe Phe Tyr Thr Pro Lys Thr Lys Arg       96
241   CTG GTA TGT GGC CGT GGT TTC TTC TAC ACT CCT AAA ACA AAG CGC       288

97   Gly Ile Val Glu Gln Cys Cys Thr Ser Ile Cys Ser Leu Tyr Gln Leu   112
289   GGC ATC GTT GAA CAG TGC TGT ACC TCT ATC TGT TCC CTG TAC CAA CTG   336

113   Glu Asn Tyr Cys Asn ***
337   GAG AAC TAC TGC AAT TAA
```

FIGURE 7

(SEQ. ID. NO. 6)

```
  1  Met Ala Thr Lys Ala Val Ser Val Leu Lys Gly Asp Gly Pro Val Gln   16
  1  ATG GCT ACT AAA GCT GTT TCT GTT TTA AAA GGT GAT GGT CCA GTT CAA   48

17  Gly Ile Ile Asn Phe Glu Gln Lys Glu Ser Asn Gly Pro Val Lys Val   32
 49  GGA ATT ATT AAT TTT GAA CAA AAA GAA AGT AAT GGA CCA GTT AAA GTA   96

33  Trp Gly Ser Ile Lys Gly Leu Thr Glu Gly Leu His Gly Phe His Val   48
 97  TGG GGA AGT ATT AAA GGA CTT ACT GAA GGC CTG CAT GGA TTC CAT GTT  144

49  His Glu Phe Gly Asp Asn Thr Ala Gly Ser Thr Ser Ala Gly Pro Arg   64
145  CAT GAG TTT GGA GAT AAT ACA GCA GGC AGT ACT AGT GCA GGT CCT CGT  192

65  Phe Val Asn Gln His Leu Cys Gly Ser His Leu Val Glu Ala Leu Tyr   80
193  TTT GTC AAC CAG CAC CTG TGT GGT TCT CAC CTG GTT GAA GCA CTG TAC  240

81  Leu Val Cys Gly Glu Arg Gly Phe Phe Tyr Thr Pro Lys Thr Arg Gly   96
241  CTG GTA TGT GGC GAA CGT GGT TTC TTC TAC ACT CCT AAA ACC CGC GGC  288

97  Ile Val Glu Gln Cys Cys Thr Ser Ile Cys Ser Leu Tyr Gln Leu Glu  112
289  ATC GTT GAA CAG TGC TGT ACC TCT ATC TGT TCC CTG TAC CAA CTG GAG  336

113  Asn Tyr Cys Asn ***
337  AAC TAC TGC AAT TAA
```

A: 5 μg of standard insulin
B: Recombinant human insulin produced following enzymatic treatment
C: Folded SOD-proinsulin hybrid polypeptide A: Standard Insulin
B: HPLC purified recombinant human insulin
C: Combined sample of HPLC purified recombinant human insulin and standard insulin

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 55 amino acids
      (B) TYPE: amino acid
      (C) STRANDEDNESS: single
      (D) TOPOLOGY: linear (ii) MOLECULE TYPE: protein (iii) HYPOTHETICAL: NO (iv) ANTI-SENSE: NO (v) FRAGMENT TYPE: N-terminal (xi) SEQUENCE DESCRIPTION: SEQ ID NO:1:

```
Asn Cys Tyr Asn Glu Leu Gln Tyr Leu Ser Cys Ile Ser Thr Cys Cys
 1               5                  10                  15

Gln Glu Val Ile Gly Arg Lys Thr Lys Pro Thr Tyr Phe Phe Gly Arg
                20                  25                  30

Glu Gly Cys Val Leu Tyr Leu Ala Glu Val Leu His Ser Gly Cys Leu
            35                  40                  45

His Gln Asn Val Phe Arg Pro
            50                  55
```

(2) INFORMATION FOR SEQ ID NO:2:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: N-terminal (xi) SEQUENCE DESCRIPTION: SEQ ID NO:2:

```
Gly Ile Val Glu Gln Cys Cys Thr Ser Ile Cys Ser Leu Tyr Gln Leu
  1               5                  10                  15

Glu Asn Tyr Cys Asn
             20
```

(2) INFORMATION FOR SEQ ID NO:3:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: N-terminal (xi) SEQUENCE DESCRIPTION: SEQ ID NO:3:

```
Thr Lys Pro Thr Tyr Phe Phe Gly Arg Glu Gly Cys Val Leu Tyr Leu
  1               5                  10                  15

Ala Glu Val Leu His Ser Gly Cys Leu His Gln Asn Val Phe
             20                  25                  30
```

(2) INFORMATION FOR SEQ ID NO:4:

(i) SEQUENCE CHARACTERISTICS:
        (A) LENGTH: 54 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: N-terminal (xi) SEQUENCE DESCRIPTION: SEQ ID NO:4:

```
Asn Cys Tyr Asn Glu Leu Gln Tyr Leu Ser Cys Ile Ser Thr Cys Cys
  1               5                  10                  15

Gln Glu Val Ile Gly Arg Thr Lys Pro Thr Tyr Phe Phe Gly Arg Glu
             20                  25                  30

Gly Cys Val Leu Tyr Leu Ala Glu Val Leu His Ser Gly Cys Leu His
             35                  40                  45

Gln Asn Val Phe Arg Pro
             50
```

(2) INFORMATION FOR SEQ ID NO:5:

(i) SEQUENCE CHARACTERISTICS:
        (A) LENGTH: 354 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: N-terminal (ix) FEATURE:
        (A) NAME/KEY: CDS
        (B) LOCATION: 1..354

(xi) SEQUENCE DESCRIPTION: SEQ ID NO:5:

```
ATG GCT ACT AAA GCC GCT AGC GTG CTG AAG GGC GAC GGC CCA GTG CAG      48
Met Ala Thr Lys Ala Ala Ser Val Leu Lys Gly Asp Gly Pro Val Gln
 1               5                  10                  15

GGC ATC ATC AAT TTC GAG CAG AAG GAA AGT AAT GGA CCA GTG AAG GTG      96
Gly Ile Ile Asn Phe Glu Gln Lys Glu Ser Asn Gly Pro Val Lys Val
            20                  25                  30

TGG GGA AGC ATT AAA GGA CTG ACT GAA GGC CTG CAT GGA TTC CAT ATT     144
Trp Gly Ser Ile Lys Gly Leu Thr Glu Gly Leu His Gly Phe His Ile
        35                  40                  45

CAT GAG TTT GGA GAT AAT ACA GCA GGC AGT ACT AGT GCA GGT CCT CGT     192
His Glu Phe Gly Asp Asn Thr Ala Gly Ser Thr Ser Ala Gly Pro Arg
    50                  55                  60

TTT GTC AAC CAG CAC CTG TGT GGT TCT CAC CTA ATT GAA GCA CTG TAC     240
Phe Val Asn Gln His Leu Cys Gly Ser His Leu Ile Glu Ala Leu Tyr
65                  70                  75                  80

CTG GTA TGT GGC GAA CGT GGT TTC TTC TAC ACT CCT AAA ACA AAG CGC     288
Leu Val Cys Gly Glu Arg Gly Phe Phe Tyr Thr Pro Lys Thr Lys Arg
                85                  90                  95

GGC ATC GTT GAA CAG TGC TGT ACC TCT ATC TGT TCC CTG TAC CAA CTG     336
Gly Ile Val Glu Gln Cys Cys Thr Ser Ile Cys Ser Leu Tyr Gln Leu
            100                 105                 110

GAG AAC TAC TGC AAT TAA                                             354
Glu Asn Tyr Cys Asn
        115
```

(2) INFORMATION FOR SEQ ID NO:6:

(i) SEQUENCE CHARACTERISTICS:
        (A) LENGTH: 352 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: N-terminal (ix) FEATURE:
        (A) NAME/KEY: CDS
        (B) LOCATION: 1..352

(xi) SEQUENCE DESCRIPTION: SEQ ID NO:6:

```
ATG GCT ACT AAA GCT GTT TCT GTT TTA AAA GGT GAT GGT CCA GTT CAA      48
Met Ala Thr Lys Ala Val Ser Val Leu Lys Gly Asp Gly Pro Val Gln
```

|   |   |   |   |   |   |   |   |   |   |   |   |   |   |   |   |     |
|---|---|---|---|---|---|---|---|---|---|---|---|---|---|---|---|-----|
| 1 |   |   |   | 5 |   |   |   |   | 10|   |   |   |   | 15|   |     |
| GGA | ATT | ATT | AAT | TTT | GAA | CAA | AAA | GAA | AGT | AAT | GGA | CCA | GTT | AAA | GTA | 96 |
| Gly | Ile | Ile | Asn | Phe | Glu | Gln | Lys | Glu | Ser | Asn | Gly | Pro | Val | Lys | Val |    |
|     |     |     | 20  |     |     |     |     |     | 25  |     |     |     | 30  |     |     |    |
| TGG | GGA | AGT | ATT | AAA | GGA | CTT | ACT | GAA | GGC | CTG | CAT | GGA | TTC | CAT | GTT | 144 |
| Trp | Gly | Ser | Ile | Lys | Gly | Leu | Thr | Glu | Gly | Leu | His | Gly | Phe | His | Val |    |
|     |     | 35  |     |     |     |     | 40  |     |     |     |     | 45  |     |     |     |    |
| CAT | GAG | TTT | GGA | GAT | AAT | ACA | GCA | GGC | AGT | ACT | AGT | GCA | GGT | CCT | CGT | 192 |
| His | Glu | Phe | Gly | Asp | Asn | Thr | Ala | Gly | Ser | Thr | Ser | Ala | Gly | Pro | Arg |    |
|     | 50  |     |     |     |     | 55  |     |     |     |     | 60  |     |     |     |     |    |
| TTT | GTC | AAC | CAG | CAC | CTG | TGT | GGT | TCT | CAC | CTG | GTT | GAA | GCA | CTG | TAC | 240 |
| Phe | Val | Asn | Gln | His | Leu | Cys | Gly | Ser | His | Leu | Val | Glu | Ala | Leu | Tyr |    |
| 65  |     |     |     |     | 70  |     |     |     |     | 75  |     |     |     |     | 80  |    |
| CTG | GTA | TGT | GGC | GAA | CGT | GGT | TTC | TTC | TAC | ACT | CCT | AAA | ACC | CGC | GGC | 288 |
| Leu | Val | Cys | Gly | Glu | Arg | Gly | Phe | Phe | Tyr | Thr | Pro | Lys | Thr | Arg | Gly |    |
|     |     |     |     | 85  |     |     |     |     | 90  |     |     |     |     | 95  |     |    |
| ATC | GTT | GAA | CAG | TGC | TGT | ACC | TCT | ATC | TGT | TCC | CTG | TAC | CAA | CTG | GAG | 336 |
| Ile | Val | Glu | Gln | Cys | Cys | Thr | Ser | Ile | Cys | Ser | Leu | Tyr | Gln | Leu | Glu |    |
|     |     |     | 100 |     |     |     |     | 105 |     |     |     |     | 110 |     |     |    |
| AAC | TAC | TGC | AAT | TAA | A   |     |     |     |     |     |     |     |     |     |     | 352 |
| Asn | Tyr | Cys | Asn | *   |     |     |     |     |     |     |     |     |     |     |     |    |
|     |     | 115 |     |     |     |     |     |     |     |     |     |     |     |     |     |    |

REFOLDING OF PROINSULINS WITHOUT ADDITION OF REDUCING AGENTS

This application is a continuation of U.S. Ser. No. 08/367,454, filed Dec. 29, 1994, now abandoned, which is a continuation-in-part of U.S. Ser. No. 08/175,298, filed Dec. 29, 1993 now abandoned.

BACKGROUND OF THE INVENTION

The disclosures of publications listed at the end of this specification immediately preceding the claims are hereby incorporated by reference in their entireties into this specification in order to more fully describe the state of the art to which this invention pertains.

Insulin is a polypeptide hormone essential for the control of glucose metabolism and it is administered daily to patients suffering from diabetes mellitus, a metabolic disorder characterized by an inadequate supply of insulin.

In vivo, the hormone is first synthesized as a long precursor molecule, subsequently processed to its biologically active form, consisting of an A and a B chain. In more detail, the gene for preproinsulin is transcribed in the beta cells of the endocrine pancreas into an mRNA precursor, which is then spliced to produce mature mRNA. This mRNA is translated into preproinsulin ($NH_2$-preregion-B chain-C peptide-A chain-COOH), which is sequentially processed into proinsulin and finally into insulin. The first step in the processing is the proteolytic elimination of the preregion, which serves as a hydrophobic signal sequence for the transfer of the nascent chain through the microsomal membranes of the rough endoplasmatic reticulum. In human preproinsulin, the length of the preregion is 24 amino acids.

In proinsulin, the two regions of the polypeptide chain that will become the mature insulin, the B- and A chains, are connected to each other by the C peptide (or C-chain), which comprises at the N and C termini two pairs of basic amino acids. In most C-peptides, these pairs are Arg-Arg and Lys-Arg. The human C peptide, including the two flanking pairs of basic amino acids, contains 35 amino acids. The C peptide connects the two portions of the polypeptide in order to aid in appropriate disulfide bridge formation between the B and A segments. Therefore the role of the C peptide does not depend greatly on its structure. In fact, its replacement by a shorter synthetic bridge still allows proper folding of the proinsulin molecule (1,2).

The proinsulin folds with the concomitant oxidation of two interchain disulfide bonds and of one disulfide bond within the A chain. In the last stage of maturation, proteolytic enzymes cleave at the basic amino acids to release the C peptide and form the mature insulin (3). In human insulin, the A chain is 21 amino acids long while the B chain is 30 amino acids long.

World demand for insulin exceeds several tons annually and there is a severe shortage of supply. Traditionally, insulin was produced from limited animal sources, mainly bovine and porcine pancreatic preparations, which differ from human insulin and may elicit an adverse immune reaction.

Studies carried out during the 1960's demonstrated in vitro production of insulin. Insulin synthesis was achieved by combining the A and B chains in their S-sulfonated forms (4) or by the spontaneous reoxidation of reduced proinsulin (5). The latter method was not practical for large scale insulin production due to very low protein concentration in the oxidation mixture. Insulin could subsequently be recovered following treatment with trypsin and carboxypeptidase B (6).

Semi-synthetic and biosynthetic (recombinant) human insulin have recently become available. Semi-synthetic human insulin is produced from porcine insulin by the trypsin catalyzed exchange of alanine with threonine at position 30 of the B chain (the only difference between porcine and human insulin). The recombinant human insulin produced either in E. coli or yeast will eventually replace all other routes of manufacture.

Biosynthetic recombinant human insulin is currently manufactured by two routes: either by producing the A and B chains separately in E.coli and subsequently combining them (7,8), or by enzymatic conversion of pro-insulin like polypeptides expressed in either E.coli (1,8) or yeast (2,9).

In most cases proinsulin is produced as a hybrid protein which accumulates as intracellular precipitated protein. This hybrid is normally purified and cleaved by CNBr in order to release the proinsulin polypeptide. The latter is further modified by oxidative sulfitolysis to proinsulin S-sulfonate. The proinsulin S-sulfonate is then purified and folded, under reducing conditions, to proinsulin (8). Conversion of the proinsulin to insulin is achieved by the combined action of trypsin and carboxypeptidase B (6).

Patent Publication No. EP 195691 B1, assigned to Novo Nordisk A/S describes a proinsulin of the formula B-Lys-Arg-A and the use thereof for the preparation of insulin in yeast.

Patent Publication No. EP 196056 Bi, assigned to Chiron Corp., describes an hSOD-proinsulin protein produced by yeast. The hSOD-proinsulin protein is subjected to cyanogen bromide cleavage and sulfitolysis prior to folding. Hoechst discloses in EPO Publication No. 379162 that 'false recombinants of insulin precursors' (i.e. recombinant insulin products with incorrect or partially incorrect intermolecular disulfide bridges) can be converted to 'correct' insulin products without sulfitolysis by reacting the false recombinants with excess mercaptan in an aqueous medium in the presence of an organic redox system. The original sulfitolysis step takes place after the amino acid or peptide radical is cleaved off (chemically or enzymatically) from the fusion polypeptide (which takes place after lysis of the host cell) since then the six cysteines of the insulin precursor are converted into their S-sulfonates. In a subsequent renaturing step, natural proinsulin is produced from this proinsulin S-sulfonate by formation of the three correct disulfide bridges. During this renaturing step, the so-called 'false recombinants' are produced.

Hoechst further discloses, in PCT International Publication No. WO 91/03550, a process for the preparation of fusion proteins containing a desired protein (e.g. proinsulin) and a "ballast constituent". Sulfitolysis is carried out before folding while the "ballast constituent" is cleaved off concomitantly with the C-chain of the proinsulin, after folding.

In addition, Hoechst describes in EP 347781 B1, a "miniproinsulin" (B-Arg-A) and the use thereof for the preparation of mono-Arg insulin and insulin. They further describe fusion proteins which comprise B-Arg-A and a "ballast constituent". The "ballast constituent" is cleaved off by cyanogen bromide and sulfitolysis is carried out before folding of the polypeptide.

The subject invention discloses recombinant human insulin production by an improved and efficient process. Recombinant proinsulin hybrid polypeptides comprising a leader sequence are synthesized in E.coli. After partial purification, they are folded with the leader peptide still attached under conditions which permit correct folding. Biologically active human insulin is then produced by combined treatment with trypsin and carboxypeptidase B in which these enzymes cleave off the leader peptide and the C-chain concomitantly. The purified human insulin thus produced is identical to naturally occurring human insulin.

The hazardous and cumbersome procedures involved in CNBr cleavage of hybrid polypeptides and sulfitolysis used to protect the abundant SH groups are excluded from this novel process since the entire proinsulin hybrid polypeptide can fold efficiently into its native structure even in the presence of the leader peptide and the unprotected cysteine residues. The active recombinant human insulin is released by enzymatic cleavage and is thereafter purified.

BRIEF DESCRIPTION OF THE FIGURES

The restriction maps for the three plasmids shown in FIGS. 3–5 do not identify all restriction sites present on these plasmids. However, those restriction sites necessary for a complete understanding of the invention, are shown.

FIG. 6: Amino acid and corresponding DNA nucleotide sequence of the SOD-proinsulin hybrid polypeptide expressed by plasmid pBAST-R. (SEQ ID NO. 5)

FIG. 7: Amino acid and corresponding DNA nucleotide sequence of the SOD-proinsulin hybrid polypeptide expressed by plasmids pDBAST-LAT and pλBAST-LAT. (SEQ ID NO. 6)

Folding of the proinsulin hybrid polypeptide (produced as described in Example 2) was performed at various pH's as indicated in 100 mM glycine buffer at 4° C. for about 16 hours with either 1 mg/ml or 0.5 mg/ml of the hybrid polypeptide. The folded material was treated with trypsin (1:500 w/w) (Sigma) and carboxypeptidase B (CPB, Sigma, 1:200 w/w) for 30 minutes at 37° at pH 9 and assayed for immunoreactive (IR) insulin by radioimmunoassay utilizing $^{125}$I-insulin (Amersham) and human recombinant insulin (Calbiochem) as standard.

Figure 9:
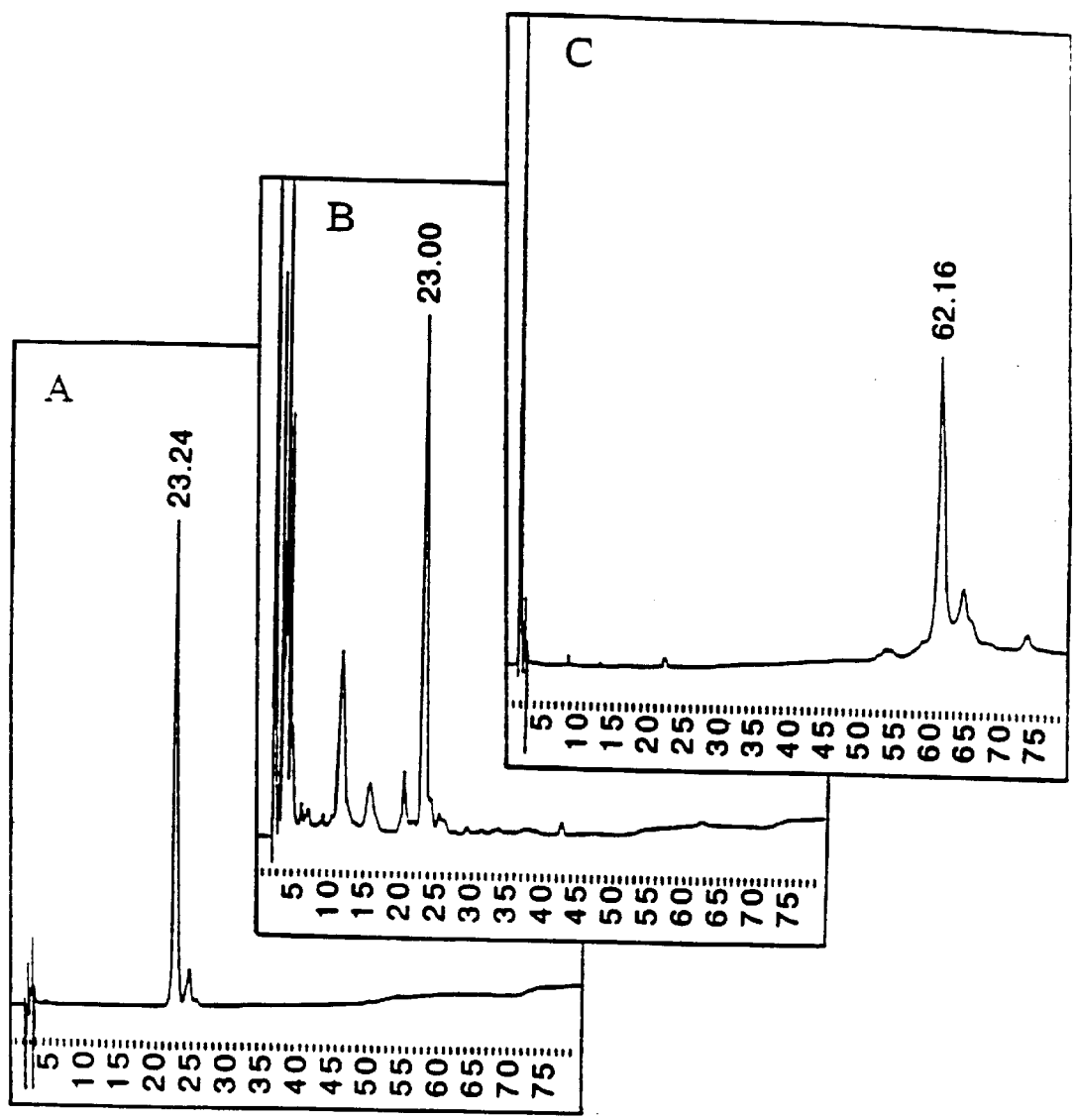

FIG. 9: Human insulin production from the proinsulin hybrid polypeptide expressed by plasmid pDBAST-LAT The proinsulin hybrid polypeptide (produced as described in Example 2) was dissolved in 8M urea, 5 mM HCl at a concentration of about 30 mg/ml and diluted to 1 mg/ml in 100 mM glycine-NaOH, pH 11.0. Folding was carried out at 22° C. (room temperature) for 20 hours. The solution was then adjusted to pH 8.8 with HCl. Carboxypeptidase B (1:1000 w/w, Sigma) and trypsin (1:2000 w/w, Sigma) were added and the reaction mixture was incubated at 37° C. for 60 minutes. Digestion mixtures were acidified to pH 3 before being diluted with 10 mM HCl. 150 μl aliquots were analyzed by Reverse Phase-High Pressure Liquid Chromatography (RP-HPLC) on a 250×4 mm, 5 μLichrosphere 100 RP-8 column (Merck) which was equilibrated with 50 mM tetraethylammonium phosphate, 162 mM NaClO$_4$, pH 3, containing 31.5% (v/v) acetonitrile. The column was developed with a linear gradient of 31.5–40.5% acetonitrile during 75 minutes at a flow rate of 1 ml/minute. Absorbance was monitored at 220 nm.

A: 5 μg of standard insulin (Boehringer-Mannheim);

B: recombinant human insulin produced following enzymatic treatment;

C: folded SOD-proinsulin hybrid polypeptide.

Figure 10:
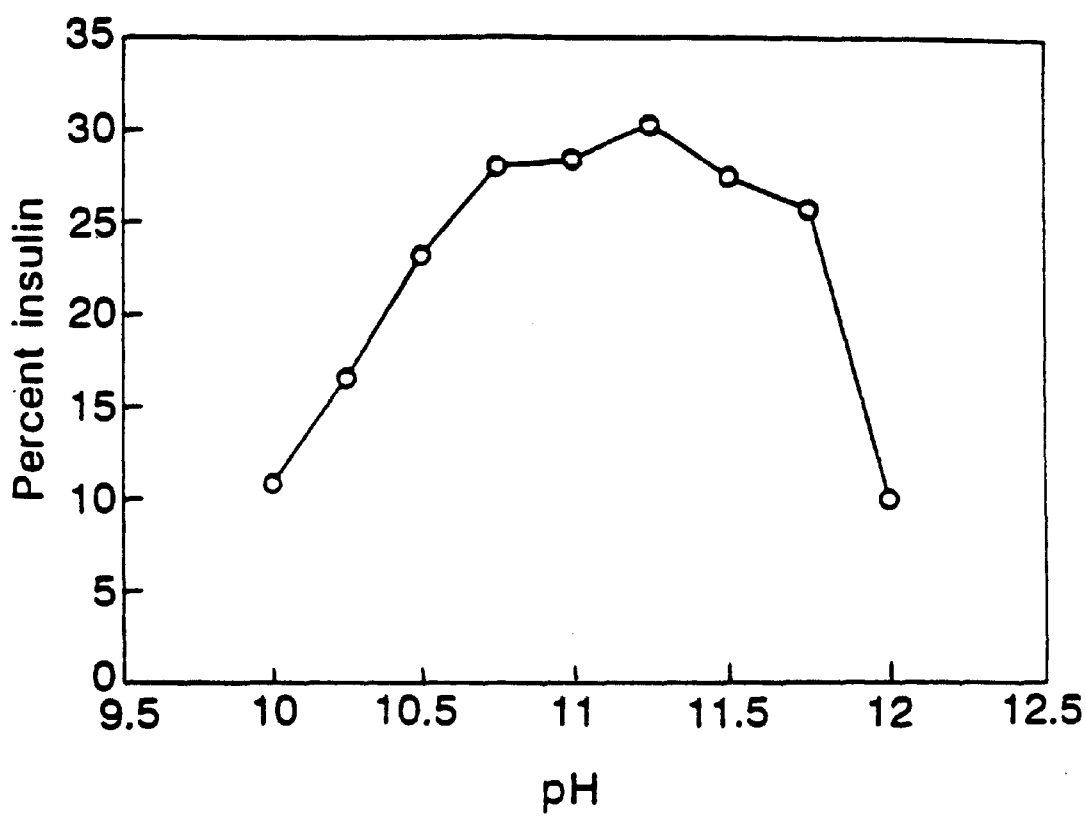

FIG. 10: Human insulin production from the proinsulin hybrid polypeptide expressed by plasmid pDBAST-LAT as a function of the pH in the folding mixture The proinsulin hybrid polypeptide (produced as described in Example 2) was diluted to 1 mg/ml in 100 mM glycine-NaOH buffer having the indicated pH values and was folded at 22° C. for 16 hours. Enzyme treatment and RP-HPLC analysis was carried out as described in FIG. 9. The amount of recombinant human insulin produced from the hybrid polypeptide was calculated according to the area of the peak which had the same retention time as standard insulin.

Figure 11:
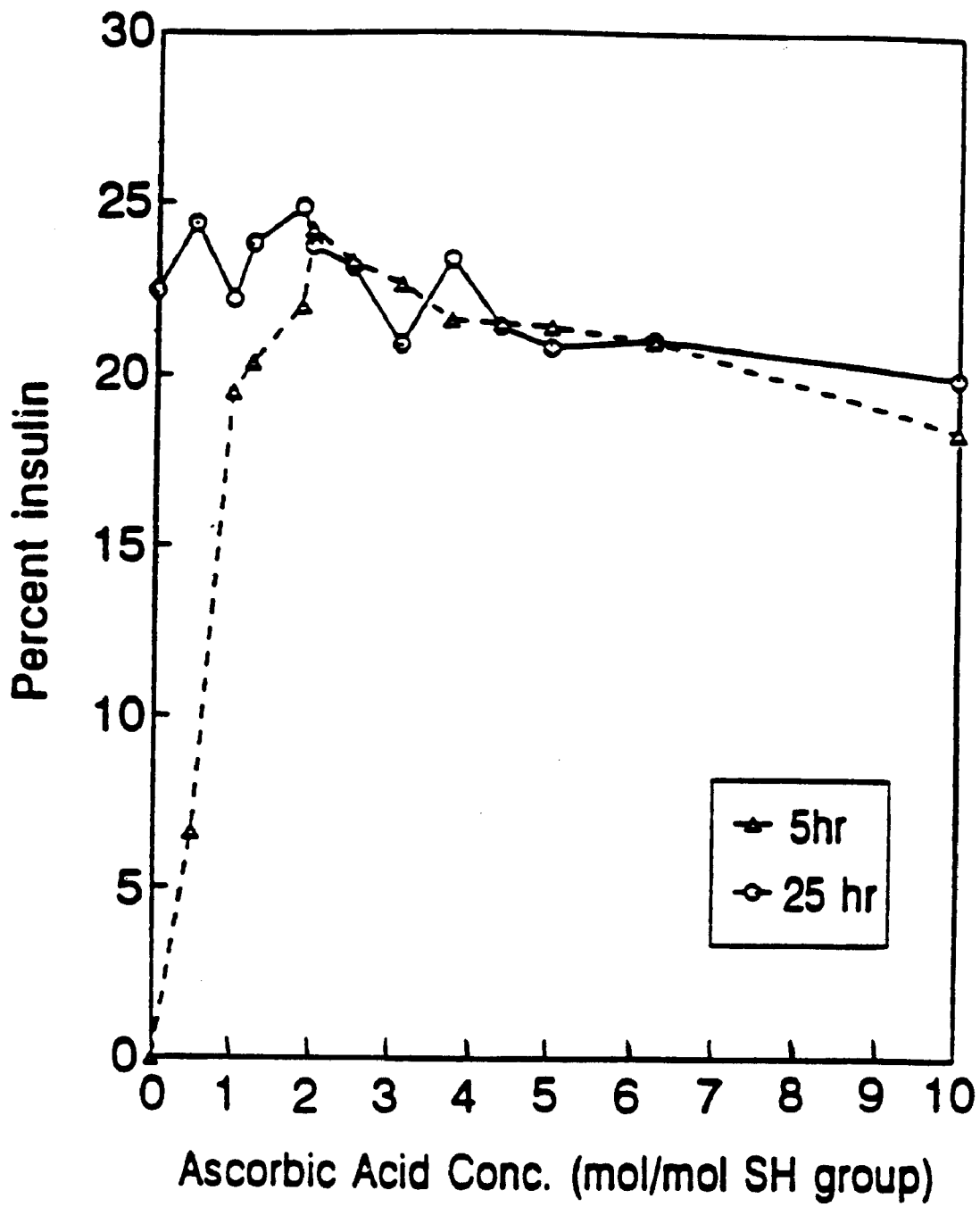

FIG. 11: Human insulin production from the proinsulin hybrid polypeptide expressed by plasmid pDBAST-LAT as a function of the ascorbic acid concentration in the folding mixture Folding of the SOD-proinsulin hybrid polypeptide (produced as described in Example 2) was carried out at 1 mg/ml in 100 mM glycine-NaOH at 22° C., pH 11.2 in the presence of the indicated concentrations of ascorbic acid. Samples were treated with trypsin and carboxypeptidase B (as in FIG. 9) after 5 and 25 hour folding periods. Recombinant human insulin production was analyzed on RP-HPLC (as in FIG. 9).

Figure 12:
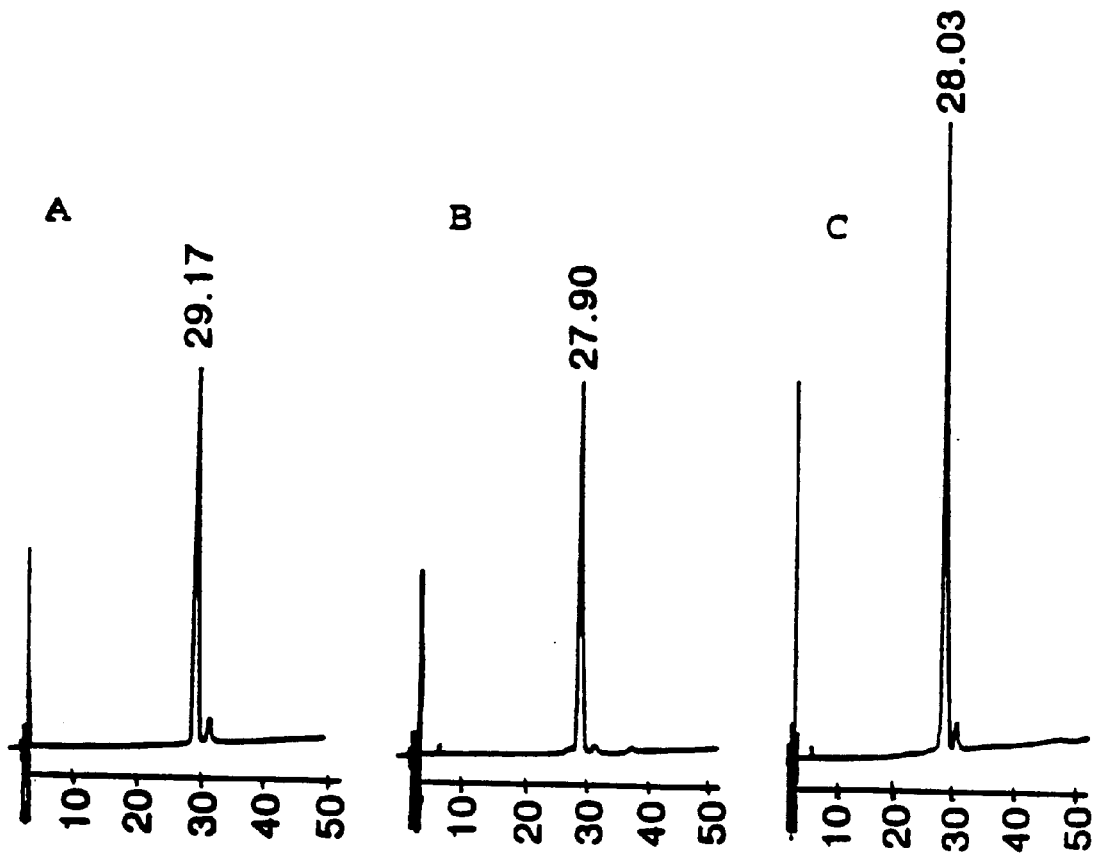

FIG. 12: Authenticity of human insulin produced from the proinsulin hybrid polypeptide expressed by plasmid pDBAST-LAT Folding of the SOD-proinsulin hybrid polypeptide (produced as described in Example 2) was carried out at 1 mg/ml in 100 mM glycine-NaOH, pH 11.2 and 1.2 mM ascorbic acid at 22° C. for 16 hours. Following enzymatic treatment (as in FIG. 9), the mixture was chromatographed on a DEAE-Sepharose column equilibrated in 20 mM Tris-HCl, pH 8. Recombinant human insulin was eluted with a linear gradient of 0–0.4M NaCl in 20 mM Tris-HCl, pH 8. Peak fractions were pooled and acidified with HCl to pH 3. The recombinant human insulin was further purified from insulin-like molecules by RP-HPLC as described for FIG. 9. The major peak was collected, desalted on Sephadex G-25 column in 0.25M Acetic acid and lyophilized. Samples (5 μg of recombinant human insulin) were prepared in 10 mM HCl and were analyzed by RP-HPLC under the same conditions.

A: Standard insulin;

B: HPLC purified recombinant human insulin

C: Combined sample of HPLC purified recombinant human insulin and standard insulin.

Figure 13:
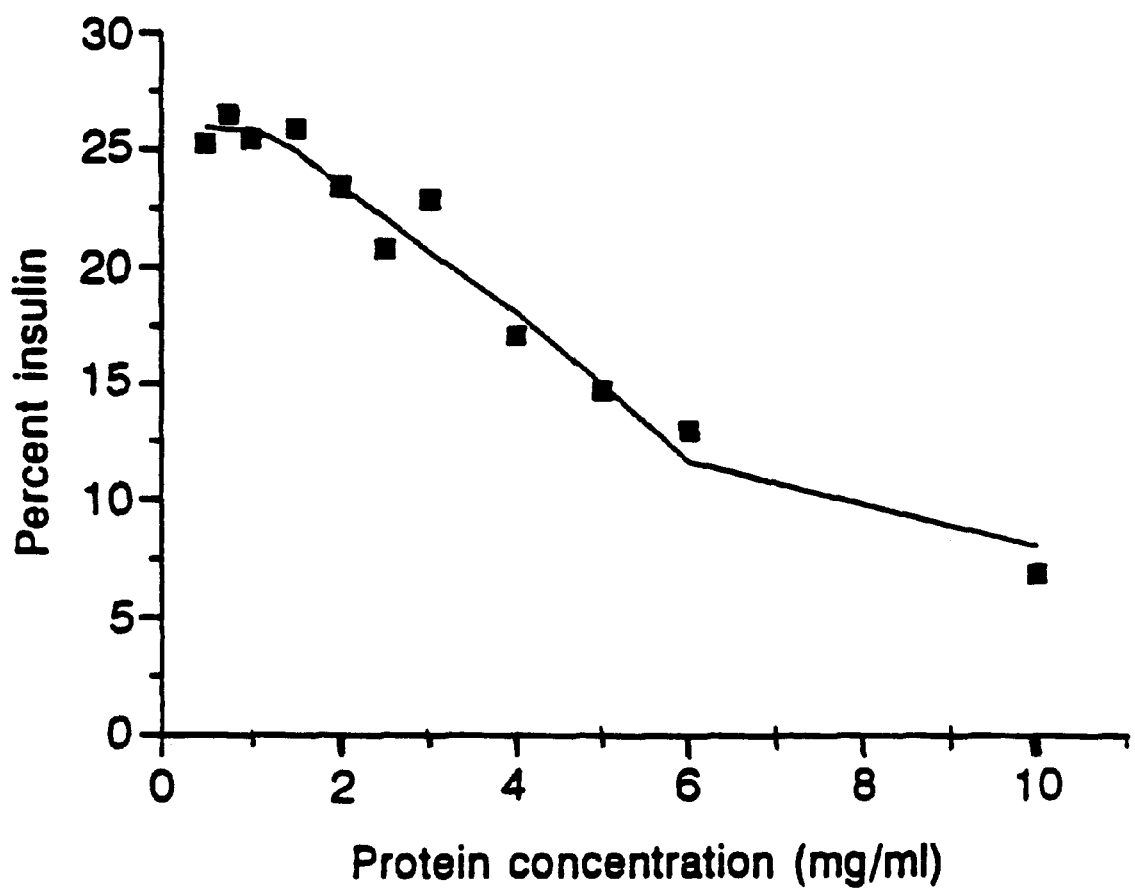

FIG. 13: Human insulin production from the proinsulin hybrid polypeptide expressed by plasmid pDBAST-LAT as a function of the protein concentration in the folding mixture SOD-proinsulin hybrid polypeptide (produced as described in Example 2) was folded in 100 mM Glycine-NaOH, pH 11.2 at a final protein concentration from 0.5 mg/ml to 10 mg/ml as indicated. Each folding mixture was supplemented with 2.5 moles ascorbic acid per mole SH group. Folding was carried out at 24° C. (room temperature) for 16 hours. Enzymatic treatment and RP-HPLC analysis were performed as described for FIG. 9.

Figure 14:
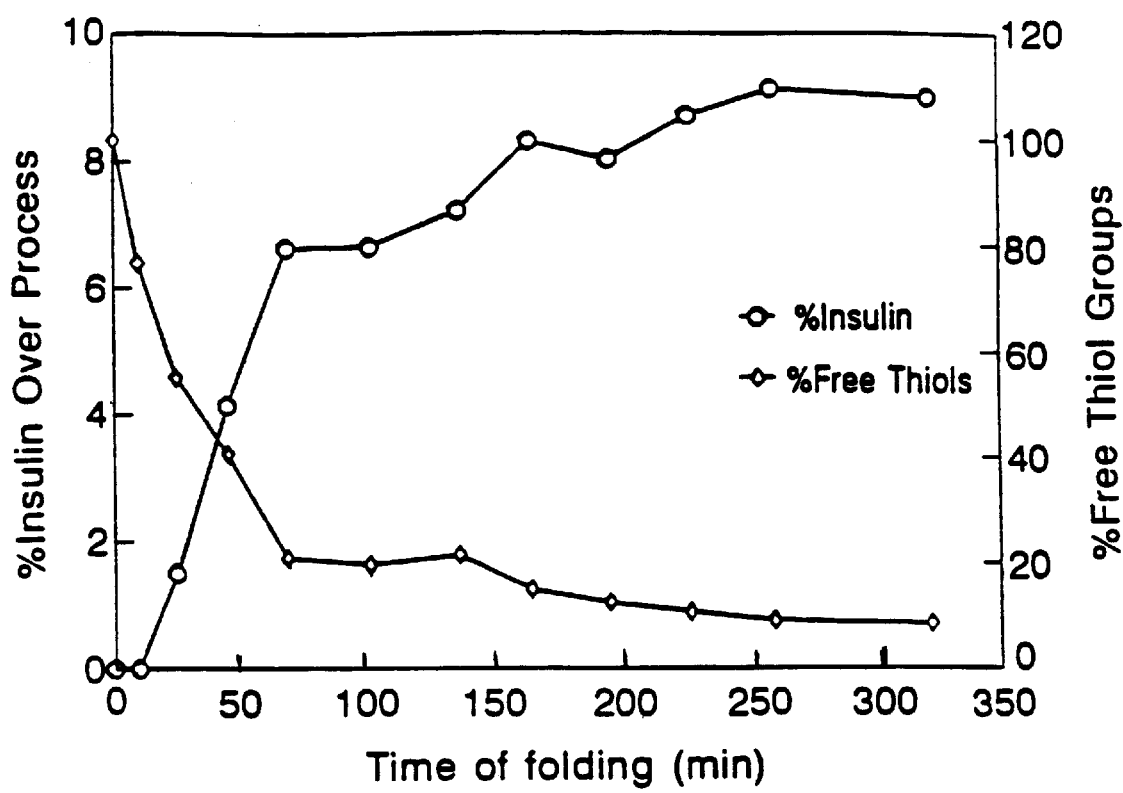

FIG. 14: Human insulin production from the proinsulin hybrid polypeptide expressed by plasmid pDBAST-LAT from crude intracellular precipitate as a function of folding time Intracellular precipitate was dissolved in 20 mM Glycine-NaOH, 33 µM EDTA, pH 11.2 at a concentration of about 2.6 $A_{280}$ per ml. The pH was adjusted to 12 with 10N sodium hydroxide. The solution was left stirring for 10 minutes. The pH was titrated to 11.2 with concentrated hydrochloric acid. Activated charcoal (acid washed, Sigma) was added to 0.1% w/v final concentration and the mixture was stirred for 30 minutes. The suspension was centrifuged (20 min., 12000 rpm) at 20° C. The clarified supernatant had an $A_{280}$ of about 2.15. Ascorbic acid was supplemented to 3 mM final concentration. Folding of the proinsulin hybrid polypeptide was carried out as shown, with vigorous stirring at room temperature (22–23° C.). At various time points along the experiment (starting from dissolution) 10 ml aliquots were withdrawn, titrated to pH 8.8 and digested with carboxypeptidase B (1:1000 w/w) and trypsin (1:2000 w/w) for 1 hour at 37° C. in the presence of 50 µM $ZnCl_2$. Digestion was terminated by acidification. Insulin content in each digested sample was determined by RP-HPLC analysis as described in FIG. 9. The progress of the folding reaction is manifested by the increase of insulin (after digestion), and the decrease in the level of free thiol groups, the latter being assayed by the Ellman reaction (16).

SUMMARY OF THE INVENTION

The subject invention provides a method of producing human insulin which comprises folding a hybrid polypeptide comprising proinsulin under conditions that permit correct disulfide bond formation, subjecting the folded, disulfide bonded hybrid polypeptide to enzymatic cleavage to produce active human insulin, and purifying the active human insulin.

The subject invention further provides a polypeptide comprising proinsulin and a leader peptide attached to the N-terminus of the proinsulin, wherein the polypeptide is folded and contains correct disulfide bonds.

DETAILED DESCRIPTION OF THE INVENTION

The plasmids pBAST-R, pDBAST-LAT and pλBAST-LAT were deposited in *E. coli* pursuant to, and in satisfaction of, the requirements of the Budapest Treaty on the International Recognition of the Deposit of Microorganisms for the Purposes of Patent Procedure with the American Type Culture Collection (ATCC), 12301 Parklawn Drive, Rockville, Md. 20852 under ATCC Accession Nos. 69362, 69361 and 69363 respectively on Jul. 26, 1993.

As used herein, a hybrid polypeptide comprises a leader peptide covalently attached to a desired polypeptide. The hybrid polypeptide of the subject invention comprises proinsulin, and preferably comprises SOD as the leader peptide.

As used herein, folding comprises folding of a hybrid polypeptide comprising proinsulin without CNBr cleavage before folding and without sulfitolysis before folding to protect SH groups, wherein the folding permits correct disulfide bond formation in the hybrid polypeptide.

As used herein, correct disulfide bond formation of the hybrid polypeptide comprises the formation of three disulfide bonds between $Cys^{B7}$—$Cys^{A7}$, $Cys^{B19}$—$Cys^{A20}$, and $Cys^{A6}$—$Cys^{A11}$ of insulin (Cys residues are numbered according to their numbering in mature insulin).

As used herein, proinsulin comprises a polypeptide comprising, from N-terminal to C-terminal order, the B, C and A chains of insulin.

As used herein, the C-chain peptide of insulin comprises the naturally-occurring C-peptide and any other oligopeptide, dipeptide or single amino acid which can be cleaved off by trypsin and carboxypeptidase B.

As used herein, a leader peptide comprises any peptide or polypeptide covalently attached to the B chain of insulin which permits folding and disulfide bond formation and which can be cleaved off by means of trypsin. The leader peptide is preferably SOD.

As used herein, SOD comprises any substantial part of the amino acid sequence of CuZnSOD or MnSOD and said part does not necessarily have the biological activity of SOD nor does it necessarily have the identical amino acid sequence of such a part compared to the amino acid sequence of naturally-occurring SOD. The DNA encoding the SOD may be mutated by methods known to those skilled in the art, e.g. Bauer et al. (1985), Gene 37: 73–81.

The leader peptide may comprise, instead of SOD, any other peptide, polypeptide or protein or any substantial part of the amino acid sequence of such a peptide, polypeptide or protein wherein said part does not necessarily have the biological activity of said peptide, polypeptide or protein nor does it necessarily have the identical amino acid sequence of such a part compared to the amino acid sequence of the naturally-occurring peptide, polypeptide or protein; however the leader peptide must permit folding and correct disulfide bond formation of the hybrid polypeptide.

As used herein, insulin may comprise a homolog of naturally occurring insulin.

As used herein, proinsulin may comprise a homolog of naturally occurring proinsulin.

As used herein, the term "homolog" relating to the insulin polypeptide produced by the methods of the subject invention, is a polypeptide which has substantially the same amino acid sequence and substantially the same biological activity as insulin. Thus, a homolog may differ from the insulin polypeptide produced by the methods of the invention by the addition, deletion, or substitution of one or more non-essential amino acid residues, provided that the resulting polypeptide retains the biological activity of insulin. Persons skilled in the art can readily determine which amino acids residues may be added, deleted, or substituted (including with which amino acids such substitutions may be made) using established well known procedures, including, for example, conventional methods for the design and manufacture of DNA sequences coding for bacterial expression of polypeptide homologs of the subject polypeptide, the modification of cDNA and genomic sequences by site-directed mutagenesis techniques, the construction of recombinant proteins and expression vectors, the bacterial expression of the polypeptides, and the measurement of the biochemical activity of the polypeptides using conventional biochemical assays.

The above definition of homologs of insulin applies equally to homologs of proinsulin.

Examples of homologs of insulin produced by the methods of the subject invention are deletion homologs containing less than all the residues of naturally-occurring insulin, substitution homologs wherein one or more residues specified are replaced by other residues, and addition homologs wherein one or more amino acids residues are added to a terminal or medial portion of the insulin polypeptide, all of which share the biological activity of insulin.

Examples of homologs are the insulin analogs disclosed in EPO Patent Application EP 384472 and also the insulin analog "Humalog" of Eli Lilly as disclosed in "Eli Lilly and Company Report to Shareholders 1992".

Substantially the same amino acid sequence is herein defined as encompassing substitutions and/or deletions and/or additions of amino acids in the amino acid sequence and may encompass up to ten (10) residues in accordance with the homologous or equivalence groups as described by e.g. Albert L. Lehninger, Biochemistry, second edition, Worth Publishers Inc. (1975), Chapter 4; Creighton, protein Structure, a Practical Approach, IRL Press at Oxford University Press, Oxford, England (1989); and Margaret 0. Dayhoff, Atlas of Protein Sequence and Structure, Volume 5, The National Biomedical Research Foundation (1972), Chapter 9. Such substitutions are known to those skilled in the art.

The DNA encoding the insulin polypeptide may be mutated by methods known to those skilled in the art, e.g. Bauer et al. (1985), Gene 37: 73–81. The mutated sequence may be inserted into suitable expression vectors as described herein, which are introduced into cells which are then treated so that the mutated DNA directs expression of the polypeptide homolog.

The plasmids of the subject invention comprising a sequence encoding a hybrid polypeptide comprising proinsulin may be adapted for expression in bacteria, yeast, fungi or mammalian cells such as CHO, chicken embryo, fibroblast or other known cell lines which additionally comprise the regulatory elements necessary for expression of the cloned gene in the bacteria, yeast, fungi or mammalian cells, so located relative to the nucleic acid encoding the hybrid polypeptide, in order to permit expression thereof. Regulatory elements required for expression include promotor sequences to bind RNA polymerase and a ribosomal binding site for ribosome binding.

The plasmids of the subject invention express a hybrid polypeptide comprising proinsulin.

Those skilled in the art will understand that the plasmids deposited in connection with this application may be readily altered by known techniques (e.g. by site-directed mutagenesis or by insertion of linkers) to encode expression of homologous polypeptides. Such techniques are described for example in Sambrook, J., Fritsch, E. F. and Maniatis, T. (1989) Molecular Cloning: A Laboratory Manual, 2nd edition, Cold Spring Harbor Laboratory Press.

The suitable regulatory elements are positioned within the plasmid relative to the DNA encoding the hybrid polypeptide comprising proinsulin, so as to effect expression of the hybrid polypeptide in a suitable host cell. In preferred embodiments of the invention, the regulatory elements are positioned close to and upstream of the DNA encoding the hybrid polypeptide.

Various ribosomal binding sites (RBS's), for rendering mRNA transcribed from DNA encoding a hybrid polypeptide comprising proinsulin capable of binding to ribosomes within the host cell, are also included in the subject invention, such as the deo RBS.

The plasmids of the invention also contain an ATG initiation codon. The DNA encoding the hybrid polypeptide comprising proinsulin is in phase with the ATG initiation codon.

The plasmids of the invention also include a DNA sequence comprising an origin of replication from a bacterial plasmid capable of autonomous replication in the host cell. Suitable origins of replication may be obtained from numerous sources, such as from plasmid pBR322 (ATCC Accession No. 37017).

The plasmids of the subject invention also include a DNA sequence which contains a gene associated with a selectable or identifiable phenotypic trait which is manifested when the plasmid is present in the host cell such as a drug resistance gene, e.g. resistance to ampicillin, chloramphenicol or tetracycline.

Examples of vectors that may be used to express the nucleic acid encoding the hybrid polypeptides (comprising proinsulin) are viruses such as bacterial viruses, e.g., bacteriophages (such as phage lambda), cosmids, plasmids and other vectors. Genes encoding hybrid polypeptides comprising proinsulin are inserted into appropriate vectors by methods well known in the art. For example, using conventional restriction endonuclease enzyme sites, inserts and vector DNA can both be cleaved to create complementary ends which base pair with each other and are then ligated together with a DNA ligase. Alternatively, synthetic linkers harboring base sequences complementary to a restriction site in the vector DNA can be ligated to the insert DNA, which is then digested with the restriction enzyme which cuts at that site. Other means are also available.

Preferred bacterial host cells are *E. coli* cells. Examples of suitable *E.coli* cells are strains Sø733 (cytRstrA) or 4300, but other *E. coli* strains and other bacteria can also be used as hosts for the plasmids.

The bacteria used as hosts may be any strain including auxotrophic (such as A1645), prototrophic (such as A4255), and lytic strains; $F^+$ and $F^-$ strains; strains harboring the cI857 repressor sequence of the $\lambda$ prophage (such as A1645 and A4255) and strains devoid of the deo repressors and/or the deo gene (see European Patent Application Publication No. 0303972, published Feb. 22, 1989). *E. coli* strain Sø733 and *E. coli* strain 4300 have been deposited under ATCC Accession Nos. 69361 and 69363 respectively.

All the *E. coli* host strains described above can be "cured" of the plasmids they harbor by methods well known in the art, e.g. the ethidium bromide method described by R. P. Novick in *Bacteriol. Review* 33, 210 (1969).

The subject invention provides a method of producing insulin which comprises folding a hybrid polypeptide comprising proinsulin under conditions that permit correct disulfide bond formation, subjecting the folded, disulfide bonded hybrid polypeptide to enzymatic cleavage to produce insulin, and purifying the insulin. The insulin has the activity and properties of commercially available human insulin.

In a preferred embodiment, the folding comprises incubating the hybrid polypeptide at about 4–37° C. for a period of about 1–30 hours at a pH of about 8.5–12.0.

In another preferred embodiment, the folding comprises incubating the hybrid polypeptide at about 4–37° C. for a period of about 1–30 hours at a pH of about 8.5–12.0 in the presence of ascorbic acid.

In an especially preferred embodiment the pH during folding is 11.0–11.25.

In another especially preferred embodiment the concentration of ascorbic acid is about 2 moles per mole SH group present in the folding mixture.

In yet another embodiment the incubation period is about 5 hours.

In another embodiment the subjecting comprises adjusting the pH to about 8.8–9.0 and cleaving the hybrid polypeptide with trypsin and carboxypeptidase B at 16–37° C. for about 30 minutes to 16 hours.

In another embodiment, the purifying comprises DEAE-Sepharose chromatography and RP-HPLC.

In yet another embodiment, the purifying further comprises ultrafiltration and CM-Sepharose chromatography.

In an especially preferred embodiment, the purifying further comprises DEAE-Sepharose chromatography and Phenyl-Sepharose chromatography.

In an especially preferred embodiment, the hybrid polypeptide is expressed by plasmid pDBAST-LAT deposited under ATCC Accession No. 69361.

In another preferred embodiment the hybrid polypeptide is expressed by plasmid pλBAST-LAT deposited under ATCC Accession No. 69363.

In another embodiment the hybrid polypeptide is expressed by plasmid pBAST-R deposited under ATCC Accession No. 69362.

In a preferred embodiment the hybrid polypeptide is obtained by treating a bacterial cell containing DNA encoding the hybrid polypeptide, so that the DNA directs expression thereof and recovering the hybrid polypeptide from the cell.

It is envisaged that the treating comprises fermentation in the presence of glucose, glycerol or galactose.

It is further envisaged that the recovery of the hybrid polypeptide from the cell comprises disrupting the cell wall of the bacterial cell or fragments thereof to produce a lysate, isolating intracellular precipitate from the lysate by centrifugation, solubilizing the precipitate and optionally purifying the hybrid polypeptide by chromatography or ultrafiltration.

The subject invention further provides a polypeptide comprising proinsulin and a leader peptide attached to the N-terminus of the proinsulin, wherein the polypeptide is folded and contains correct disulfide bonds.

In a preferred embodiment the leader peptide is derived from the N-terminus of CuZnSOD.

In an especially preferred embodiment the leader peptide comprises 62 amino acids, being preceded by the amino acid Met and followed by an Arg residue.

In a preferred embodiment the proinsulin comprises the insulin B-chain linked to the insulin A chain by a single Arg residue.

In another embodiment, the proinsulin comprises the insulin B-chain linked to the insulin A chain by the dipeptide Lys-Arg.

The above two proinsulin molecules have to be produced as hybrid proteins, otherwise expression levels are extremely low and not of commercial significance.

In all preferred embodiments the cysteine residues of the leader peptide have been replaced by serine residues.

EXAMPLES

The Examples which follow are set forth to aid in understanding the invention but are not intended to, and should not be construed to, limit its scope in any way. The Examples do not include detailed descriptions for conventional methods employed in the construction of vectors, the insertion of genes encoding polypeptides into such vectors or the introduction of the resulting plasmids into hosts. The Examples also do not include detailed description for conventional methods employed for assaying the polypeptides produced by such host vector systems. Such methods are well known to those of ordinary skill in the art and are described in numerous publications including by way of example the following:

Sambrook, J., Fritsch, E. F. and Maniatis, T. (1989) *Molecular Cloning: A Laboratory Manual,* 2nd edition, Cold Spring Harbor Laboratory Press.

Example 1

Construction of Production Plasmids pBAST-R, pDBAST-LAT and pλBAST-LAT Expressing SOD-proinsulin Hybrid Polypeptides Bacterial expression vectors, which overproduce hybrid proteins in *E. coli,* under the control of either the deo $P_1P_2$ or $\lambda P_L$ promoter, were constructed. Proinsulin was produced as a hybrid protein since it was found that bacteria harboring an expression vector encoding Insulin B-chain-Lys-Arg-Insulin A-chain produced no detectable polypeptide. The hybrid proteins comprise a leader peptide, 62 amino acids long, derived from the N-terminus of CuZnSOD (11), preceded at the N-terminus by a Met residue and followed at the C-terminus by an Arg residue linking it to insulin B-chain. The insulin B-chain is linked to insulin A-chain by a short C-chain peptide consisting of Lys-Arg or Arg. The two cysteines originally present in the SOD portion were replaced by serine residues.

A. Plasmid pBAST-R

A series of plasmids was constructed culminating in pBAST-R, which upon transformation of the proper *E. coli* host cells was capable of directing efficient expression of a proinsulin hybrid polypeptide useful for human insulin production.

Figure 3:
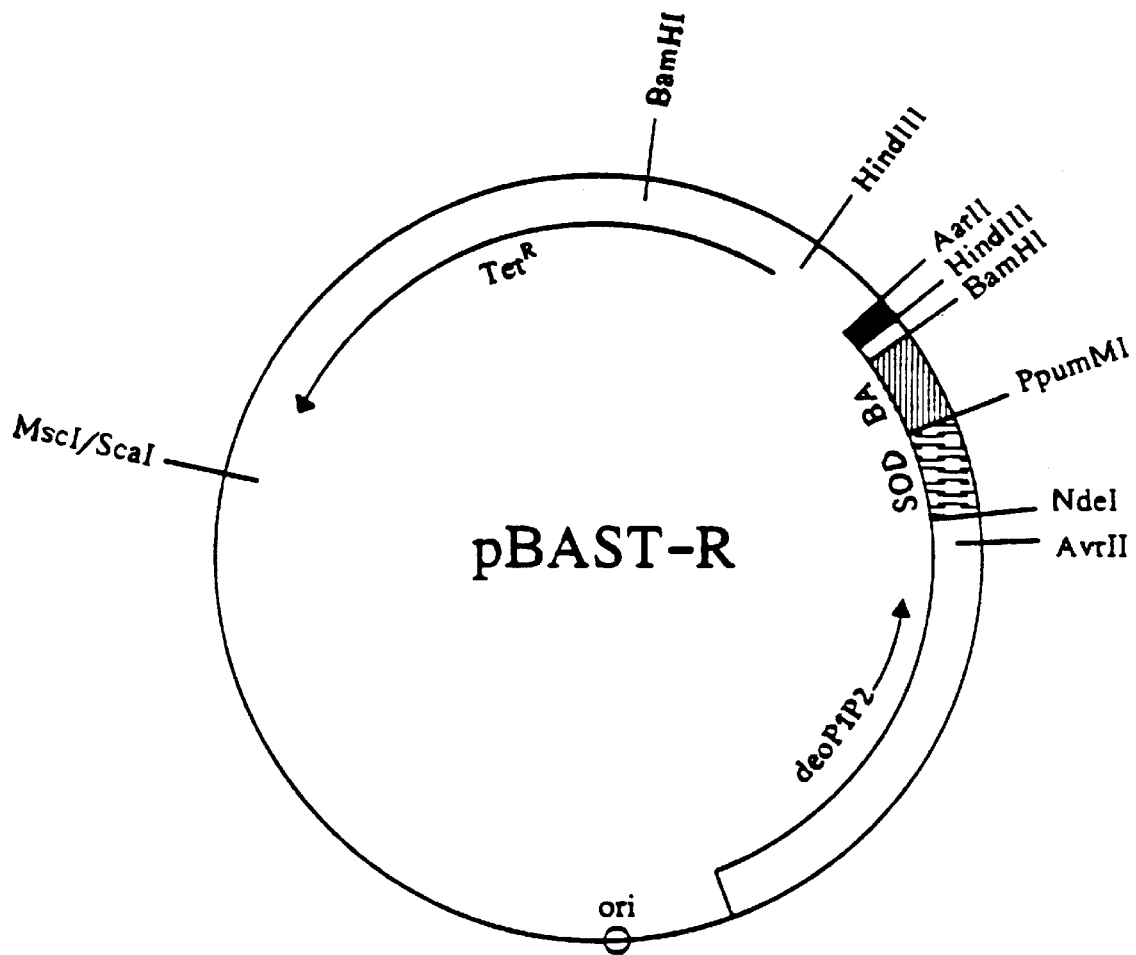
FIG. 3: Structure of plasmid pBAST-R, an expression plasmid encoding an SOD-proinsulin hybrid polypeptide deposited with the ATCC under ATCC Accession No. 69362.

The structure of plasmid pBAST-R, encoding SOD-Insulin B chain-Lys-Arg-Insulin A chain hybrid polypeptide is shown in FIG. 3; the DNA sequence and corresponding amino acid sequence of the hybrid polypeptide are shown in FIG. 6.

Plasmid pBAST-R is about 4380 bp long and comprises the following elements (in a counterclockwise direction):

1. A DNA fragment, 1521 bp long, spanning AatII-MscI sites on pBR322 which includes the tetracycline resistance gene.
2. A DNA fragment, 1497 bp long, spanning ScaI-HaeII sites on pBR322 which includes a truncated ampicillin resistance gene and the origin of DNA replication.
3. A DNA fragment, 930 bp long, spanning AvaII-NdeI sites on *E. coli* DNA which includes the deo $P_1P_2$ promoters and ribosomal binding site (RBS)(13).
4. A DNA fragment, 188 bp long, spanning NdeI-PpuMI sites of human CuZnSOD cDNA. The cysteines at positions 6 and 57 of mature SOD were substituted with serine residues by oligonucleotide site-directed mutagenesis (Yanofsky et al.) (12).
5. A synthetic DNA fragment, 172 bp long, with PpuMI and BamHI ends. This region encodes Arg-insulin B chain-Lys-Arg-insulin A chain.
6. A synthetic 36 bp multiple cloning site polylinker with BamHI and HindIII ends.
7. A synthetic 44 bp oligonucleotide containing the TrpA transcription terminator with HindIII and AatII ends (10).

Plasmid pBAST-R, which confers tetracycline resistance and which encodes the SOD-Insulin B chain-Lys-Arg- Insulin A chain hybrid polypeptide, was introduced into *E. coli* strain Sø733 (cytRstrA) and deposited in the ATCC under ATCC Accession Number 69362 on Jul. 26, 1993.

B. Plasmid pDBAST-LAT

Another series of plasmids was constructed culminating in plasmid pDBAST-LAT, which upon transformation of the proper *E. coli* host cells was capable of directing efficient high level expression of a proinsulin hybrid polypeptide useful for human insulin production.

Figure 4:
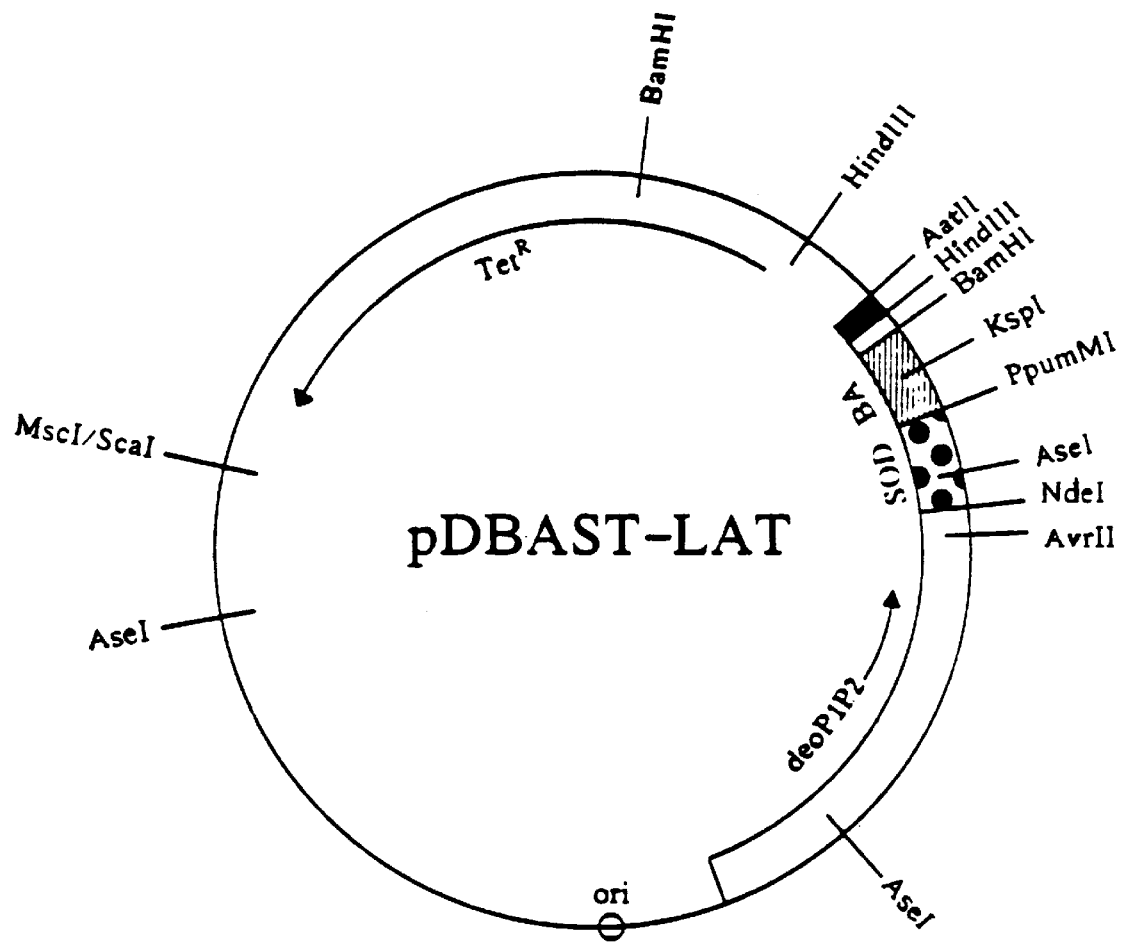
FIG. 4: Structure of pDBAST-LAT, an expression plasmid encoding an SOD-proinsulin hybrid polypeptide deposited with the ATCC under ATCC Accession No. 69361.

The structure of plasmid pDBAST-LAT, encoding SOD-Insulin B chain-Arg-Insulin A chain hybrid polypeptide is shown in FIG. 4; the DNA sequence and corresponding amino acid sequence of the hybrid polypeptide are shown in FIG. 7. Plasmid pDBAST-LAT is about 4377 bp long and comprises the following elements (in a counterclockwise direction):

1. A DNA fragment, 1521 bp long, spanning AatII-MscI sites on pBR322 which includes the tetracycline resistance gene.
2. A DNA fragment, 1497 bp long, spanning ScaI-HaeII sites on pBR322 which includes a truncated ampicillin resistance gene and the origin of DNA replication.
3. A DNA fragment, 930 bp long, spanning AvaII-NdeI sites on *E. coli* DNA which includes the deo $P_1P_2$ promoters and RBS (13).
4. A DNA fragment, 188 bp long, spanning NdeI-PpuMI sites of human CuZnSOD cDNA. The cysteines at positions 6 and 57 of mature SOD were substituted with serine residues and the GC content of this fragment was reduced to 38% by oligonucleotide site-directed mutagenesis (12).
5. A synthetic DNA fragment, 169 bp long, with PpuMI and BamHI ends. This region encodes Arg-insulin B chain-Arg-insulin A chain.
6. A synthetic 36 bp multiple cloning site polylinker with BamHI and HindIII ends.
7. A synthetic 44 bp oligonucleotide containing the TrpA transcription terminator with HindIII and AatII ends (Yanofsky et al.) (10).

Plasmid pDBAST-LAT, which confers tetracycline resistance and which encodes the SOD-Insulin B chain-Arg-Insulin A chain hybrid polypeptide, was introduced into *E. coli* strain Sø733 (cytRstrA) and deposited in the ATCC under ATCC Accession Number 69361 on Jul. 26, 1993.

C. Plasmid pλBAST-LAT

Another series of plasmids was constructed culminating in plasmid pλBAST-LAT, which upon transformation of genetically engineered *E. coli* host cells (harboring the cI857 repressor) was capable of directing efficient expression of a proinsulin hybrid polypeptide useful for human insulin production.

Figure 5:
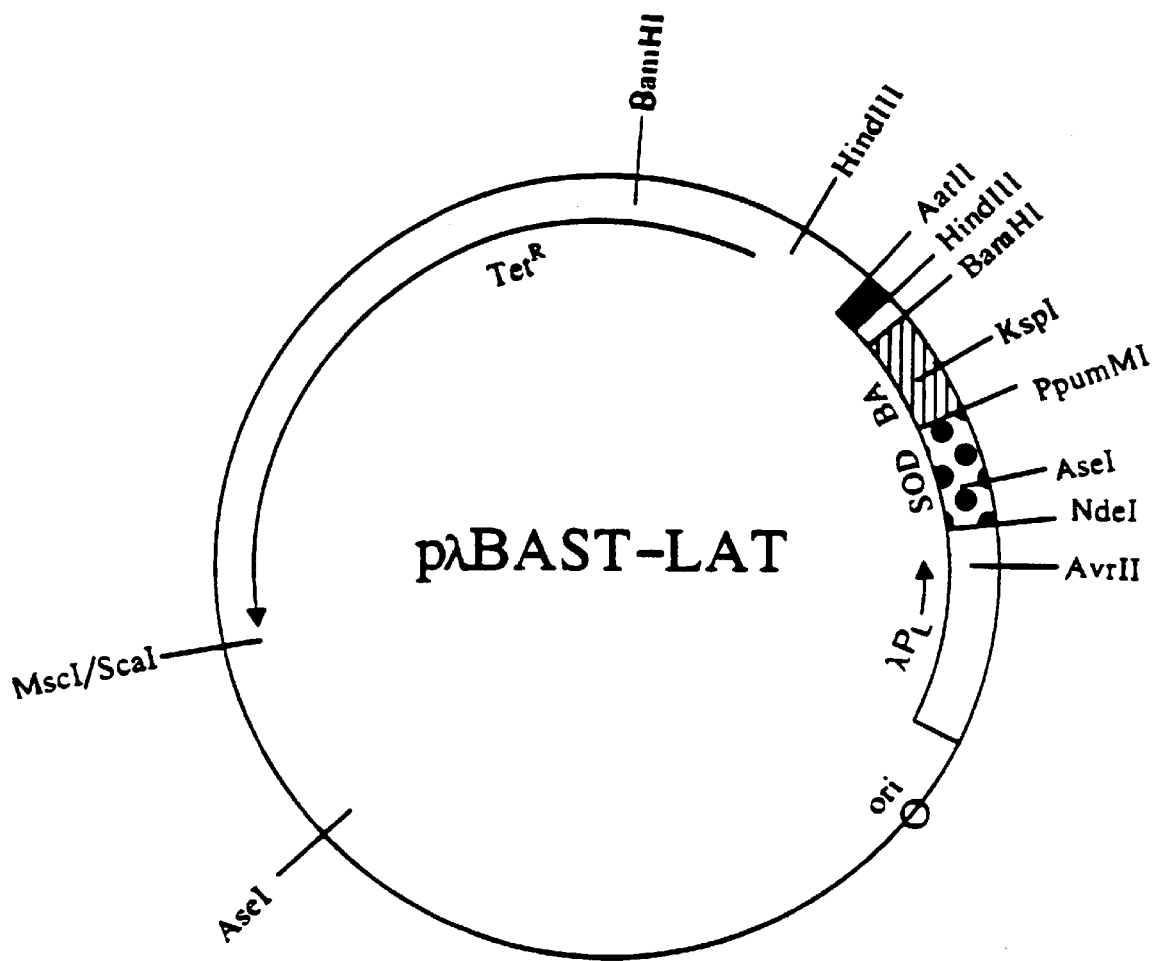
FIG. 5: Structure of pλBAST-LAT, an expression plasmid encoding an SOD-proinsulin hybrid polypeptide deposited with the ATCC under ATCC Accession No. 69363.

The structure of plasmid pλBAST-LAT, encoding SOD-Insulin B chain-Arg-Insulin A chain hybrid polypeptide is shown in FIG. 5. The DNA sequence and corresponding amino acid sequence of the hybrid polypeptide are shown in FIG. 7.

Plasmid pλBAST-LAT is about 3777 bp long and comprises the following elements (in a counterclockwise direction):

1. A DNA fragment, 1521 bp long, spanning AatII-MscI sites on pBR322 which includes the tetracycline resistance gene.
2. A DNA fragment, 1497 bp long, spanning ScaI-HaeII sites on pBR322 which includes a truncated ampicillin resistance gene and the origin of DNA replication.
3. A DNA fragment, 330 bp long, spanning BamHI-EcoRI sites on plasmid pSODα13 (14) which includes the λ$P_L$ promoter and an AvrII-NdeI 30 base pair long deo ribosomal binding site.
4. A DNA fragment, 188 bp long, spanning NdeI-PpuMI sites of human CuZnSOD cDNA. The cysteines at positions 6 and 57 of mature SOD were substituted with serine residues and the GC content of this fragment was reduced to 38% by oligonucleotide site-directed mutagenesis (12).
5. A synthetic DNA fragment, 169 bp long, with PpuMI and BamHI ends. This region encodes Arg-insulin B chain-Arg-insulin A chain.
6. A synthetic 36 bp multiple cloning site polylinker with BamHI and HindIII ends.
7. A synthetic 44 bp oligonucleotide containing the TrpA transcription terminator with HindIII and AatII ends (10).

Plasmid pλBAST-LAT, which confers tetracycline resistance and which encodes the SOD-Insulin B chain-Arg-Insulin A chain hybrid polypeptide under the control of the λ$P_L$ promoter, was introduced into *E. coli* strain 4300 (F-, bio, cI$^{857}$) and deposited in the ATCC under ATCC Accession No. 69363 on Jul. 26, 1993.

Bacterial cells were propagated at 30° C. Production of the hybrid polypeptide was induced upon temperature shift to 42° C.

Example 2

Fermentation, Growth Conditions and Purification of SOD-proinsulin Hybrid Polypeptides I. Stock Cultures Stock culture of *E. coli* strain Sø733 harboring plasmid pDBAST-LAT (or pBAST-R) was grown on casein medium (20gr/L casein hydrolysate, 10 gr/l yeast extract and 5gr/L NaCl) supplemented with tetracycline (10 mg/L). The cultures were then diluted two-fold with freezing medium and stored at −80° C.

Freezing medium:

| | |
|---|---|
| $K_2HPO_4$ | 6.3 gr |
| $KH_2PO_4$ | 1.8 gr |
| Na Citrate | 0.45 gr |
| $MgSO_4.7H_2O$ | 0.09 gr |
| $(NH_4)_2SO_4$ | 0.9 gr |
| Glycerol | 44 gr |
| Per 500 ml | |

II. Inoculum

The inoculum was propagated in production medium (see below). Sterile medium in a shake flask was inoculated from stock culture and incubated 15 hours on a shaker at 37° C. and approximately 200 r.p.m. If needed, subsequent stages in inoculum propagation were carried out in stirred aerated fermenters. Sterile medium was inoculated with 2–10% flask culture, and incubated 15 hours at 37° C., pH 7±0.5 with agitation and aeration to maintain the dissolved oxygen level above 20% air saturation.

III. Production

Production medium:

| | |
|---|---|
| $K_2HPO_4$ | 8 gr/L |
| $KH_2PO_4$ | 2 gr/L |
| Na citrate | 2 gr/L |
| $NH_4Cl$ | 3 gr/L |

-continued

| | |
|---|---|
| $K_2SO_4$ | 0.6 gr/L |
| $FeSO_4.7H_2O$ | 0.04 gr/L |
| $MgSO_4.7H_2O$ | 0.4 gr/L |
| $CaCl_2.2H_2O$ | 0.02 gr/L |
| Trace elements solution | 3 ml/L |
| Tetracycline | 0.01 gr/L |
| Glucose | 2 gr/L |
| Glycerol | 1 ml/L |

Trace elements solution:

| | |
|---|---|
| $MnSO_4.H_2O$ | 1 gr/L |
| $ZnSO_4.7H_2O$ | 2.78 gr/L |
| $CoCl_2.7H_2O$ | 2 gr/L |
| $Na_2MoO_4.2H_2O$ | 2 gr/L |
| $CaCl_2.2H_2O$ | 3 gr/L |
| $CuSO_4.5H_2O$ | 1.85 gr/L |
| $H_3BO_3$ | 0.5 gr/L |
| HCl (32%) | 100 ml/L |

The production medium was inoculated with 0.5–10% inoculum culture and incubated at 37° C. Agitation-aeration rates were set to maintain the dissolved oxygen level above 20% air saturation. The pH was maintained at 7±0.2 with $NH_3$.

Sterile solutions of 50% glucose and 30% glycerol were infused to supply energy and carbon sources. Once cell concentration reached an $OD_{660}$ of 25, sterile solutions of 10% glucose and 30% glycerol were infused and growth continued for about 5 hours until cell concentration reached an approximate $OD_{660}$ of 60. The culture was then chilled and cells were recovered by centrifugation. Fermentation of *E. coli* in the presence of any one of glucose, glycerol, galactose or a combination thereof as carbon source facilitated the expression of the SOD-proinsulin hybrid polypeptides.

IV. Purification

The SOD-proinsulin hybrid polypeptides expressed by plasmids pBAST-R and pDBAST-LAT accumulated in intracellular precipitate which was isolated by the following procedure: 1 gr (wet weight) of bacterial cake was suspended in 10 ml buffer containing 50 mM Tris-HCl, pH 8, 10 mM EDTA and was treated with lysozyme (Merck, 2500 u/ml) at 37° C. for 2 hours. The mixture was then sonicated and Nonidet-P-40 (Sigma) or Tritonx100 was added to a final concentration of 2% and stirred for 2 hours at room temperature. The precipitate was pelleted by centrifugation and washed with water.

The hybrid polypeptide was purified to near homogeneity by anion exchange chromatography as follows. The precipitate was dissolved in 8M urea, 20 mM Tris-HCl, 200 mM β-mercaptoethanol, pH 8.2. The solution was clarified by centrifugation and chromatographed on DEAE-Sepharose Fast-Flow column (Pharmacia LKB), pre-equilibrated in 8M Urea, 20 mM Tris-HCl, 20 mM β-mercaptoethanol, pH 8.2. Flow-through material was collected and the hybrid protein was either precipitated with $(NH_4)_2SO_4$ at 40% saturation or concentrated by ultrafiltration on 10K membrane followed by diafiltration against 100 mM Glycine-HCl, pH 3.1.

Alternatively, the SOD-proinsulin hybrid polypeptide expressed by plasmid pBAST-R was purified to near homogeneity by dissolution in 8M urea, 20 mM Dithiothreitol, 50 mM NaAcetate, pH 5, and by ultrafiltration through a series of 100 kD and 50 kD membranes (Filtron). The hybrid polypeptide was concentrated on a 10 kD membrane and precipitated with $(NH_4)_2SO_4$ at 40% saturation.

Example 3

Folding and Enzymatic Cleavage of the SOD-proinsulin Hybrid Polypeptides

Proinsulin hybrid polypeptides, obtained by $(NH_4)_2SO_4$ precipitation or by ultrafiltration (Example 2), were dissolved in 8M urea, 5 mM HCl and diluted into 100 mM glycine buffer, pH 8.5–12.0 at a final concentration of about 1 mg/ml.

A. Folding of the SOD-proinsulin hybrid polypeptide expressed by plasmid pBAST-R took place at about 4–37° C. for a period of about 1–24 hours in order to permit correct disulfide bond formation.

The pH of the solution containing the folded, disulfide bonded hybrid polypeptide was adjusted to about 8.8–9.0 with HCl and the protein was treated with trypsin and carboxypeptidase B at 16–37° C. for 30–120 minutes.

Figure 8:
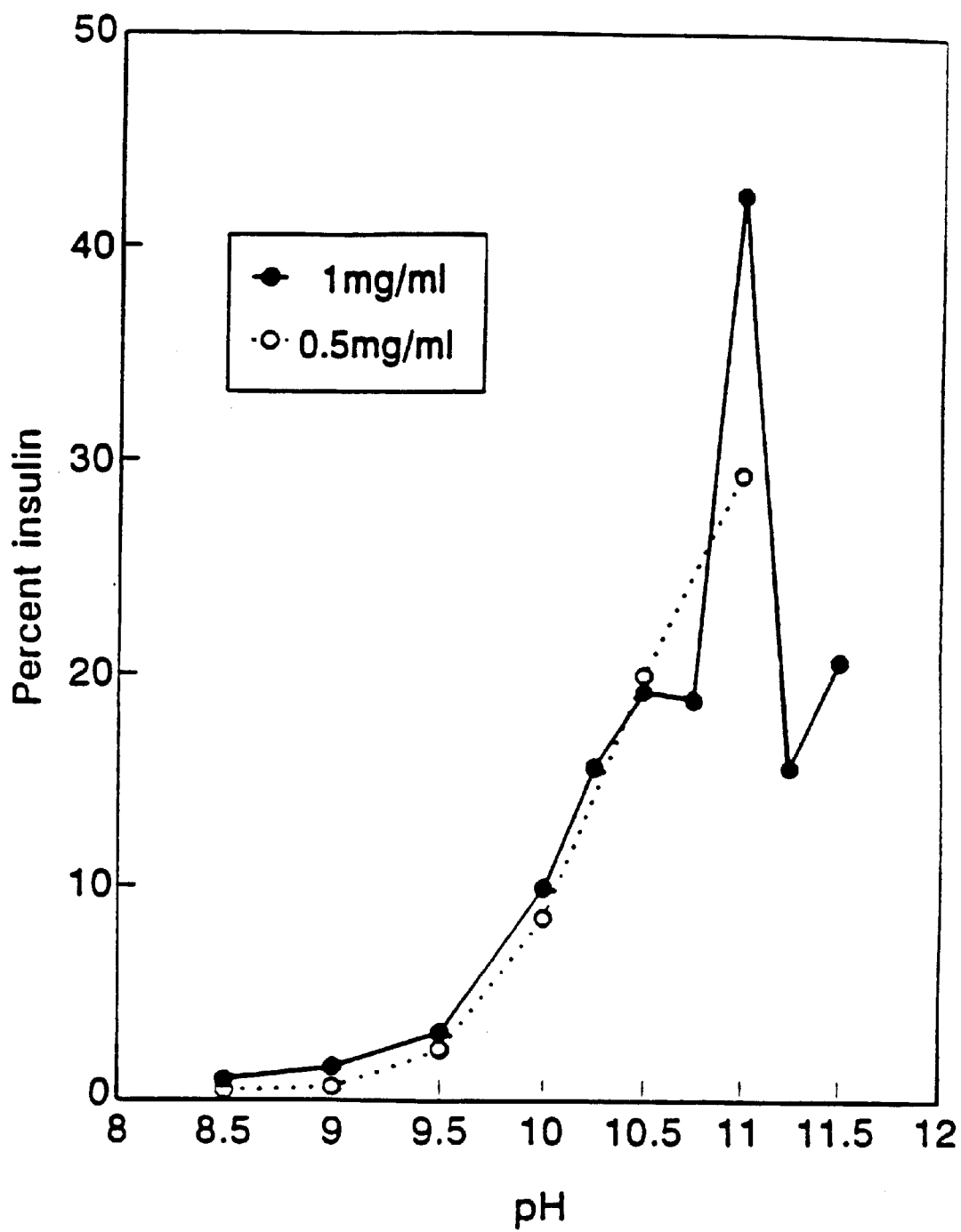
FIG. 8: Human insulin production, from the proinsulin hybrid polypeptide expressed by plasmid pBAST-R, as a function of the pH of the folding mixture.

After considerable experimentation, it was found that the optimal conditions were as follows: The hybrid polypeptide expressed by plasmid pBAST-R was dissolved in 8M urea, 5 mM HCl and diluted into 100 mM glycine buffer, pH 11.0 (FIG. 8) at a final concentration of about 1 mg/ml, after which folding of the hybrid polypeptide took place for 6–16 hours at 25° C., whereafter the folded, disulfide bonded hybrid polypeptide was cleaved with trypsin (1:500 w/w) and carboxypeptidase B (1:200 w/w) at 37° C. for 30–60 minutes.

Figure 1:
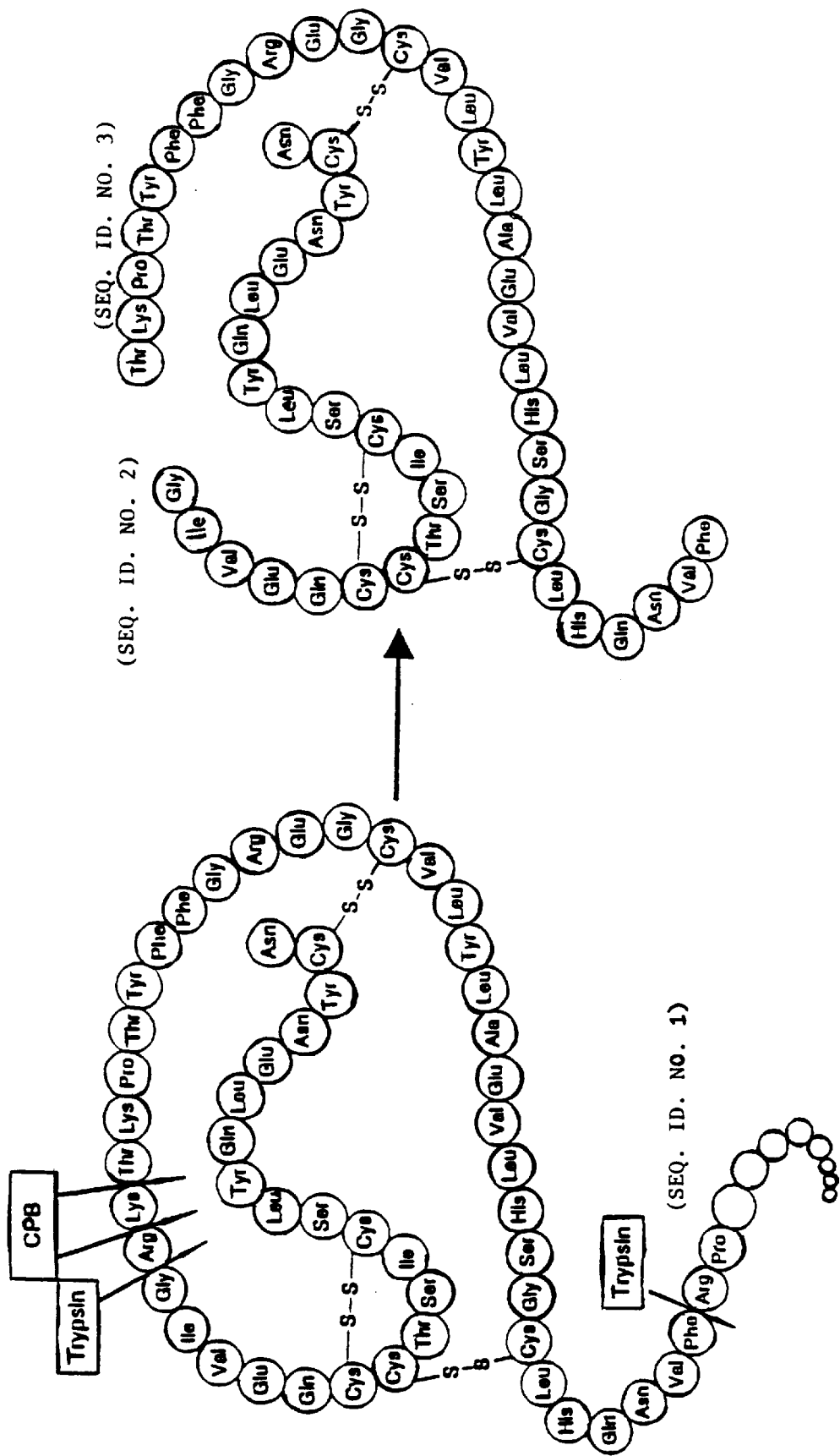
FIG. 1: Human insulin generation by enzymatic cleavage of the folded, disulfide bonded proinsulin hybrid polypeptide produced by expression of plasmid pBAST-R. Only part of the SOD leader sequence is indicated. (SEQ ID NOS. 1, 2 and 3)

Insulin generation by enzymatic cleavage of the folded disulfide bonded proinsulin hybrid polypeptide expressed by plasmid pBAST-R is diagrammatically shown in FIG. 1.

B. Folding of the SOD-proinsulin hybrid polypeptide expressed by plasmid pDBAST-LAT took place at about 7–31° C. for a period of about 5–30 hours in order to permit correct disulfide bond formation.

The pH of the solution containing the folded, disulfide bonded hybrid polypeptide was adjusted to about 8.8–9.0 with HCl and the protein was treated with trypsin and carboxypeptidase B at 22–37° C. for 30 minutes to 16 hours.

After considerable experimentation, it was found that the optimal conditions were as follows: The hybrid polypeptide expressed by plasmid pBAST-R was dissolved in 8M urea, 5 mM HCl and diluted into 100 mM glycine buffer, pH 11.0–11.25 (FIG. 8) at a final concentration of about 1 mg/ml, after which folding of the hybrid polypeptide took place for 5 hours at 25° C., whereafter the folded, disulfide bonded hybrid polypeptide was cleaved with trypsin (1:15.000 w/w) and carboxypeptidase B (1:10.000 w/w) at 25° C. for 16 hours.

Figure 2:
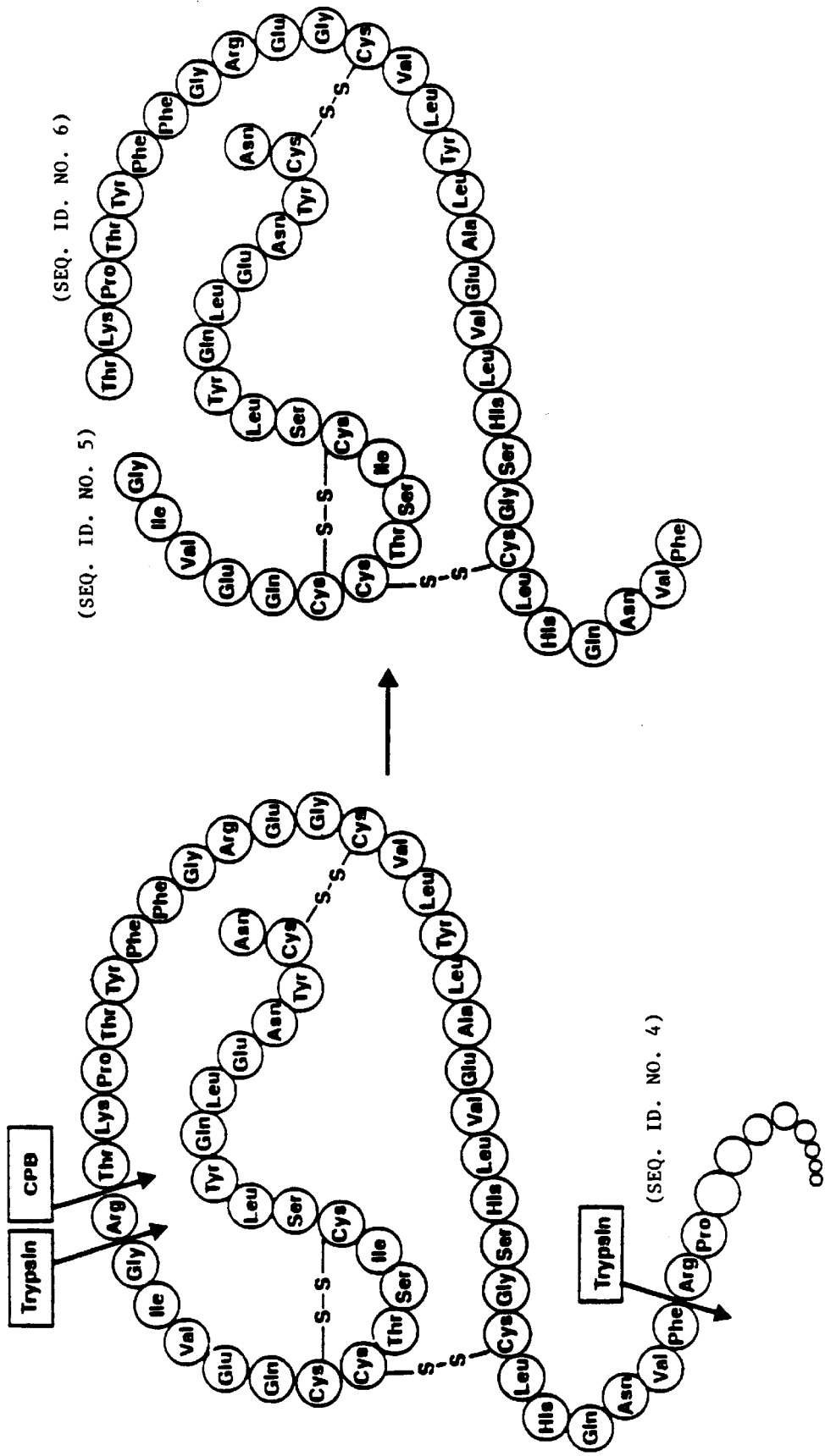
FIG. 2: Human insulin generation by enzymatic cleavage of the folded, disulfide bonded proinsulin hybrid polypeptide produced by expression of plasmid pDBAST-LAT or plasmid pλBAST-LAT. Only part of the SOD leader sequence is indicated. (SEQ ID NOS. 2, 3 and 4)

Insulin generation by enzymatic cleavage of the folded disulfide bonded proinsulin hybrid polypeptide expressed by plasmid pDBAST-LAT is diagrammatically shown in FIG. 2.

Examples of specific conditions for both A and B above are detailed in the legends to FIGS. 8–14.

Example 4

Protein Analysis and Purification of Human Insulin from the SOD-proinsulin Hybrid Polypeptide Expressed by Plasmid pBAST-R Human insulin generation from the SOD-proinsulin hybrid polypeptide expressed by plasmid pBAST-R was determined by radioimmunoassay and RP-HPLC, utilizing commercial human insulin as standard (Calbiochem). The theoretical yield of recombinant human insulin as calculated according to the amino acid sequence of the proinsulin hybrid polypeptide is 45.6%. It is evident from FIG. 8 that optimal folding occurs at pH 11. At this pH value, insulin production amounts to about 80% of the theoretical yield (which corresponds to about 40% of the input hybrid polypeptide). Human insulin produced from the proinsulin hybrid polypeptide expressed by plasmid pBAST-R, was detected by RP-HPLC. A Vydac 218TP54, 250×4.6 mm I.D. (Separation Group), 5 μm, 300 Å pore size column was used at room temperature with a flow rate of 1 ml/min. 0.1% Trifluoroacetic acid (TFA) in $H_2O$ was used as eluant A and 0.08% TFA in acetonitrile as eluant B. The column was washed for 5 minutes in equilibration buffer (25% eluant B) followed by a linear gradient of 25–50% eluant B during 37.5 minutes. Absorbance was monitored at 220 nm or at 280 nm. Analysis of the human insulin following the enzymatic digestion of the folded, disulfide bonded hybrid polypeptide using Reverse Phase-High Pressure Liquid Chromatography revealed a major peak with the same retention time as standard human insulin.

Two small scale batches were prepared yielding 26 mg and 13 mg of human insulin respectively. Human insulin was purified from the enzyme-treated solution (pH 9) by ultrafiltration on either 3K or 5K membranes (Filtron) followed by CM-Sepharose chromatography (citrate buffer, pH 3). Peak fractions were desalted, lyophilized and subjected to N-terminal sequencing and amino acid analysis. The amino acid composition of both batches of recombinant human insulin was essentially identical to naturally-occurring human insulin (see Table 1, preparation 1). The sequence of 5 amino acids at the amino terminus of the insulin preparations was determined by Edman degradation. It was found to be identical to the $NH_2$-terminus of both the A and B chain of human insulin, which confirms the authenticity of the in vitro product.

However, the sequencing results indicated the presence of an extra Arg residue at the first position in about 25% of the molecules. This result corresponds to trypsin cleavage between Lys and Arg, inside the linker sequence Lys-Arg, thus leaving an additional Arg residue on the amino terminus of the A-chain.

It was found that specific hydrolysis at the C-terminal of Arg by trypsin can be achieved by performing the reaction at pH 11. At this elevated pH, most of the E -amino groups of Lys are not charged (pK=10.3) thus enabling selective cleavage. Two batches yielding 1 mg and 6.5 mg of purified insulin were obtained by carrying out the trypsin step at pH 11 (see Table 1, preparation 2) followed by carboxypeptidase B digestion at pH 8.5. N-terminal sequencing revealed that the amount of insulin comprising an extra Arg was reduced to about 5%.

TABLE 1

Amino Acid Composition of Recombinant Human Insulin

| Amino Acid | Theoretical | Standard Insulin | Preparation 1 | Preparation 2 |
|---|---|---|---|---|
| Asx | 3 | 3.20 | 3.38 | 3.26 |
| Thr | 3 | 2.98 | 2.83 | 2.68 |
| Ser | 3 | 2.84 | 2.53 | 2.77 |

TABLE 1-continued

Amino Acid Composition of Recombinant Human Insulin

| Amino Acid | Theoretical | Standard Insulin | Preparation 1 | Preparation 2 |
|---|---|---|---|---|
| Glx | 7 | 7.15 | 7.73 | 7.23 |
| Pro | 1 | 1.28 | 1.13 | 1.09 |
| Gly | 4 | 4.24 | 4.39 | 4.25 |
| Ala | 1 | 1.00 | 1.28 | 1.04 |
| Cys | 6 | 5.88 | 5.11 | 5.79 |
| Val | 4 | 3.82 | 4.58 | 3.88 |
| Ile | 2 | 2.04 | 1.96 | 1.96 |
| Leu | 6 | 5.87 | 6.10 | 5.99 |
| Tyr | 4 | 3.80 | 3.80 | 3.87 |
| Phe | 3 | 3.15 | 3.56 | 3.03 |
| His | 2 | 2.04 | 2.05 | 2.08 |
| Lys | 1 | 1.01 | 1.05 | 1.02 |
| Arg | 1 | 0.96 | 1.30 | 1.18 |

Preparation 1 and 2 show the amino acid composition of recombinant human insulin produced from the proinsulin hybrid polypeptide expressed by plasmid pBAST-R. Trypsin cleavage was carried out either at pH 9 (preparation 1) or at pH 11 (preparation 2).

Amino acid analysis was performed after performic acid oxidation and gas phase hydrolysis of purified insulin preparations.

Example 5

Peptide Analysis of Purified Human Insulin Produced from the SOD-proinsulin Hybrid Polypeptide Expressed by Plasmid pBAST-R Purified human insulin produced as described in the above Examples, was subjected to peptide analysis utilizing endoproteinase Glu-C (Sigma), which hydrolyzes peptide bonds at the carboxyl side of glutamyl residues.

In more detail, insulin samples (100 μg), produced by cleavage of the folded, disulfide bonded proinsulin hybrid polypeptide expressed by plasmid pBAST-R, were digested with 5 μg Glu-C for 6 hrs at 37° C. in 100 μl of 0.1 M Tris-HCl, pH 7.8. HPLC analysis was performed: samples of commercially available (control) insulin and insulin produced by cleavage of the folded, disulfide bonded proinsulin hybrid polypeptide expressed by plasmid pBAST-R were acidified to a pH of about 3 and were separated by RP-HPLC. A Vydac 218TP54, 250×4.6 mm I.D., 5 μm, 300 Å pore size column was used. The column was equilibrated with 50 mM tetraethylammonium phosphate, 162 mM $NaClO_4$, pH 3, containing 31.5% (v/v) acetonitrile and was developed with a linear gradient of 35–45% acetonitrile during 75 minutes at a flow rate of 1 ml/minute. Absorbance was monitored at 220 nm.

All expected peptides were generated in agreement with the control reaction even though a minor shoulder following the peak corresponding to one of the fragments is probably related to des-Thr($B_{30}$) insulin-like molecule (15).

Examples 4 and 5 indicate that the recombinant polypeptide expressed by plasmid pBAST-R comprises the sequence of naturally-occurring human insulin. A minor portion of the recombinant protein produced comprised forms such as Arg(Ao), desamido- or des-Thr($B_{30}$) insulin-like molecules. These unwanted by-products can be eliminated by chromatographic procedures such as RP-HPLC as described above.

Example 6

Protein Analysis and Purification of Human Insulin Produced from the Proinsulin Hybrid Polypeptide Expressed by Plasmid pDBAST-LAT In order to avoid generation of Arg(Ao) insulin by-product (Examples 4 and 5), expression plasmid pBAST-R was modified to comprise DNA coding only for an Arg residue between the A and B chains of the proinsulin hybrid polypeptide as opposed to DNA coding for Lys-Arg between the A and B chains of the proinsulin hybrid polypeptide expressed by plasmid pBAST-R. This resulted in expression plasmids pDBAST-LAT (Example 1B) and pλBAST-LAT (Example 1C).

Efficient production of insulin occurred following folding and enzymatic treatment with trypsin and CPB of the folded, disulfide bonded proinsulin hybrid polypeptide expressed by new expression plasmid pDBAST-LAT. The presence of insulin-like contaminants was low (FIG. 9). Folding was optimal at pH 11.25 (FIG. 10) and was significantly enhanced in the presence of about 2 moles ascorbic acid per mole SH group in the reaction mixture (FIG. 11).

The effect of protein concentration on the yield of insulin produced from proinsulin hybrid polypeptide was determined in a series of reactions under otherwise optimal folding conditions. Optimal yields were obtained when protein concentration did not exceed 1.5 mg/ml (FIG. 13).

The insulin was purified by DEAE-Sepharose chromatography followed by RP-HPLC (as described in FIG. 9). As is evident from FIG. 12, the recombinant human insulin produced had the same retention time as standard (commercially available) human insulin. The amino acid composition of the purified recombinant human insulin preparation is identical to standard insulin (see Table 2, recombinant insulin).

Note that Table 2 indicates that the insulin produced from the proinsulin hybrid polypeptide expressed by plasmid pDBAST-LAT did not have the extra Arg residue attached to the insulin A chain (Arg (Ao) insulin) as described in Example 4. Thus the preferred plasmid for production of insulin is plasmid pDBAST-LAT and the preferred sequence for the proinsulin hybrid polypeptide is that shown in FIG. 7.

TABLE 2

Amino Acid Composition of Recombinant Human Insulin

| Amino Acid | Theoretical | Number of residues Standard Insulin | Recombinant insulin |
|---|---|---|---|
| Asx | 3 | 3.20 | 3.32 |
| Thr | 3 | 2.98 | 2.73 |
| Ser | 3 | 2.84 | 2.71 |
| Glx | 7 | 7.15 | 7.41 |
| Pro | 1 | 1.28 | 1.02 |
| Gly | 4 | 4.24 | 4.46 |
| Ala | 1 | 1.00 | 1.09 |
| Cys | 6 | 5.88 | 5.28 |
| Val | 4 | 3.82 | 4.00 |
| Ile | 2 | 2.04 | 1.91 |
| Leu | 6 | 5.87 | 6.34 |
| Tyr | 4 | 3.80 | 3.64 |
| Phe | 3 | 3.15 | 3.06 |
| His | 2 | 2.04 | 2.18 |
| Lys | 1 | 1.01 | 1.02 |
| Arg | 1 | 0.96 | 1.07 |

The amino acid composition of standard human insulin and recombinant human insulin produced from the proinsulin hybrid polypeptide expressed by plasmid pDBAST-LAT are shown.

Amino acid analysis was performed after performic acid oxidation and gas phase hydrolysis of purified insulin preparations.

Example 7

Human Insulin Production from the Proinsulin Hybrid Polypeptide Expressed by Plasmid pDBAST-LAT from Crude Intracellular Precipitate An improved method for folding and enzymatic conversion of the proinsulin hybrid polypeptide to insulin was carried out by using crude intracellular precipitate, omitting the need for the initial purification step as described in Example 2, part IV. Efficient production of insulin occurred following enzymatic cleavage of the folded, disulfide bonded proinsulin hybrid polypeptide with trypsin and carboxypeptidase B (FIG. 14 and Table 3). Insulin yields were calculated as the percent of initial protein concentration ($A_{280}$) as determined at the precipitate dissolution step at pH 12 (FIG. 14). Folding of SOD-proinsulin hybrid polypeptide from crude intracellular precipitate was shown to be optimal at about 4.5 hours from the start of the experiment (FIG. 14).

Table 3 summarizes the partial purification of insulin from the proinsulin hybrid polypeptide expressed by plasmid pBAST-LAT from crude intracellular precipitate prepared from one liter fermentation culture at an $O.D._{660}$ of 45. Dissolution and folding were carried out as described for FIG. 14. At 4.5 hours from dissolution, the folded bulk solution including the folded, disulfide bonded proinsulin hybrid polypeptide was titrated to pH 8.8 with concentrated hydrochloric acid. $ZnCl_2$ (to 50 $\mu$M final concentration), carboxypeptidase B (1:4000 w/w) and trypsin (1:6000 w/w) were added. Digestion was performed for 3 hours at 37° C. and was terminated by addition of phenylmethylsulfonyl fluoride (PMSF) to 0.5 mM final concentration. Analysis by HPLC (as described in FIG. 9) indicated an insulin yield of 169 mg. Insulin was purified by a sequence of anion-exchange and hydrophobic chromatographic steps. Digested folding mixture was loaded on DEAE Sepharose Fast Flow (Pharmacia) column pre-equilibrated in 20 mM Tris-HCl, 10 mM NaCl pH 8 buffer at about 50 $A_{280}$ units per ml resin. Bound material was washed with 20 mM Tris-HCl, 100 mM NaCl, pH 8 buffer and insulin eluted with 250 mM NaCl in the same buffer. Pool fractions containing insulin represented 20% of loaded protein and had a purity of 37.1%. Ammonium sulfate was added to the DEAE elution pool to a concentration of 410 mM and was loaded on Phenyl-Sepharose Fast Flow column pre-equilibrated in 20 mM Tris HCl, 540 mM Ammonium sulfate at about 12 $A_{280}$ units per ml resin. Bound material was washed with equilibration buffer and insulin eluted with 20 mM Tris HCl, 220 mM ammonium sulphate, pH 8 buffer. Fractions containing insulin represented 42.3% of loaded protein and had a purity of 74.1%. As a result of this partial purification process, 120 mg insulin, identical to standard insulin, was produced which corresponds to an insulin yield of 5.16%. Further purification of insulin may be carried out by use of methods known in the art, e.g. gel filtration, RP-HPLC and crystallization (17).

TABLE 3

Purification of recombinant human insulin, produced from the proinsulin hybrid polypeptide expressed by plasmid pDBAST-LAT, following dissolution of crude intracellular precipitate, folding and enzymatic treatment with trypsin and carboxypeptidase B.

| Purification step | $A_{280}$ | minimum amount of insulin by HPLC - in mg | % purity |
|---|---|---|---|
| Precipitate dissolution | 2326 | — | — |
| Charcoal treatment | 1915 | — | — |
| Folding and enzymatic treatment | 1915 | 169 | 8.8 |
| DEAE-Sepharose pool | 383 | 142 | 37.1 |
| Phenyl-Sepharose pool | 162 | 120 | 74.1 |

$A_{280}$ represents the total absorbance at 280 nm at each purification step. Insulin presence was determined by HPLC analysis relative to standard insulin as described for FIG. 9 and corresponds to the major insulin peak of standard insulin.

REFERENCES

Cousens, L. S., Shuster, J. R., Gallegos, C., Ku, L., Stempien, M. M., Urdea, M. S., Sanchez-Pescador, R., Taylor, A. and TeKamp-Olson, P., Gene 61: 265–275, 1987.

Davidson, H. W., Rhodes, C. J. and Hutton, J. C., Nature 333: 93–96, 1988.

Ellman, G. L., Arch. Biochem. Biophys. 82:70–77, 1959.

Fischer, M., Fytlovitch, S., Amit, B., Wortzel, A. and Beck, Y., Appl. Microbiol. Biotechnol. 33: 424–428, 1990.

Frank, B. H. and Chance, R. E. (1985), The preparation and characterization of human insulin of recombinant DNA origin, in Therapeutic agents produced by genetic engineering, Quo Vadis Symposium, Sanofi Group, May 29–30, 1985, Toulouse-Labege, France, pp:137–146.

Goeddel, D. V., Kleid, D. G., Bolivar, F., Heyneker, H. L., Yansura, D. G., Crea, R., Hirose, T., Kraszewski, A., Itakura, K. and Riggs, A. D., Proc. Natl. Acad. Sci. 76: 106–110, 1979.

Grau, U., Diabetes 34:1174–1180, 1985.

Hartman, et al., U.S. Pat. No. 5,143,836, Sep. 1, 1992.

Kemmler, W., Peterson, J. D. and Steiner, D. F., J. Biol. Chem. 246: 6786–6791, 1971.

Morinaga, Y., Franceschini, T., Inouye, S. and Inouye, M., Biotechnology 2:636–639, 1984.

Panayotis, G., Katsoyannis, G. and Tometsko, A., Proc. Natl. Acad. Sci. U.S.A., 55:1554–1561, 1966.

Schlichtkrull, J., Acta Chem. Scand. 10:1459–1464, 1956.

Sherman, L., Dafni, L., Liehman-Hurwitz, J. and Groner, Y., Proc. Natl. Acad. Sci. 80: 5465–5469, 1983.

Steiner, D. F. and Clark, J. L., Proc. Natl. Acad. Sci. 60:622–629, 1968.

Thim, L., Hansen, M. T., Norris, K., Hoegh, I., Boel, E., Forstrom, J., Ammerer, G. and Fiil, N. P., Proc. Natl. Acad. Sci. U.S.A., 83:6766–6770, 1986.

Wetzel, R., Kleid, D. G., Crea, R., Heyneker, H. L., Yansura, D. G., Hirose, T., Kraszewski, A., Riggs, A. D., Itakura, K. and Goeddel, D. V., Gene 16:63–71, 1981.

Yanofsky, C., Platt, T., Crawford, I. P., Nichols, B. P., Christie, G. E., Horowitz, H., Van Cleemput, M. and Wu, A. M., Nucleic Acids Res. 9:6647–6668, 1981.

What is claimed is:

1. A method of producing insulin which comprises:
   (a) obtaining a hybrid polypeptide comprising proinsulin by treating a bacterial cell containing DNA encoding the hybrid polypeptide, so that the hybrid polypeptide is expressed and is recovered from the cell;
   (b) folding the hybrid polypeptide without first subjecting the hybrid polypeptide to sulfitolysis under conditions that permit correct disulfide bond formation in absence of exogenous reducing agent;
   (c) subjecting the resulting folded, disulfide bonded hybrid polypeptide to enzymatic cleavage to produce insulin; and
   (d) purifying the insulin so produced.

2. A method according to claim 1 wherein step (b) further comprises incubating the hybrid polypeptide at about 4–37° C. for a period of about 1–30 hours at a pH of about 8.5–12.0.

3. A method according to claim 2 wherein the pH is 11.0–11.25.

4. A method according to claim 2 wherein the incubation period is about 5 hours.

5. A method according to claim 1 wherein step (c) further comprises:
   (i) adjusting the pH to about 8.8–9.0; and
   (ii) cleaving the hybrid polypeptide with trypsin and carboxypeptidase B at 16–37° C. for 30 minutes to 16 hours.

6. A method according to claim 1 wherein step (d) further comprises purification by means of DEAE-Sepharose chromatography and RP-HPLC.

7. A method according to claim 1 wherein step (d) further comprises purification by means of ultrafiltration and CM-Sepharose chromatography.

8. A method according to claim 1 wherein step (d) further comprises purification by means of DEAE-Sepharose chromatography and Phenyl-Sepharose chromatography.

9. A method according to claim 1 wherein the proinsulin hybrid polypeptide is expressed by plasmid pDBAST-LAT deposited under ATCC Accession No. 69361.

10. A method according to claim 1 wherein the proinsulin hybrid polypeptide is expressed by plasmid pλBAST-LAT deposited under ATCC Accession No. 69363.

11. A method according to claim 1 wherein the proinsulin hybrid polypeptide is expressed by plasmid pBAST-R deposited under ATCC Accession No. 69362.

12. A method according to claim 1 wherein the treating in step (a) comprises fermentation in the presence of glucose, glycerol or galactose.

13. A method according to claim 1 wherein the recovery in step (a) comprises:
   (i) disrupting the cell wall of the bacterial cell or fragments thereof to produce a lysate;
   (ii) isolating intracellular precipitate from the lysate by centrifugation; and
   (iii) solubilizing the precipitate.

* * * * *